US011957390B2

(12) United States Patent
Sidebotham et al.

(10) Patent No.: US 11,957,390 B2
(45) Date of Patent: Apr. 16, 2024

(54) SURGICAL BONE SCREW METHOD AND APPARATUS

(71) Applicant: BioMedtrix, LLC, Whippany, NJ (US)

(72) Inventors: Christopher G. Sidebotham, Mendham, NJ (US); Gregory Thomas Van Der Meulen, Ketchum, ID (US)

(73) Assignee: BioMedtrix, LLC, Whippany, NJ (US)

( * ) Notice: Subject to any disclaimer, the term of this patent is extended or adjusted under 35 U.S.C. 154(b) by 413 days.

(21) Appl. No.: 17/148,375

(22) Filed: Jan. 13, 2021

(65) Prior Publication Data

US 2021/0212740 A1 Jul. 15, 2021

Related U.S. Application Data

(60) Provisional application No. 62/960,540, filed on Jan. 13, 2020.

(51) Int. Cl.
*A61B 17/86* (2006.01)
(52) U.S. Cl.
CPC ........ *A61B 17/8625* (2013.01); *A61B 17/862* (2013.01)
(58) Field of Classification Search
CPC .................... A61B 17/8863; B23D 29/02–023
See application file for complete search history.

(56) References Cited

U.S. PATENT DOCUMENTS

| 6,780,115 | B2 | 8/2004 | Schmieding et al. |
| 8,496,690 | B2 | 7/2013 | Sixto et al. |
| 9,072,559 | B2 | 7/2015 | Appenzeller et al. |
| 9,757,171 | B2 | 9/2017 | Sixto et al. |
| 10,245,086 | B2 | 4/2019 | Treace et al. |
| 2008/0103500 | A1* | 5/2008 | Chao ............... A61B 17/8863 606/84 |
| 2014/0090527 | A1* | 4/2014 | Behlen ............... B26B 13/00 83/13 |

FOREIGN PATENT DOCUMENTS

| EP | 2477573 | 7/2015 |
| WO | WO 2006076729 | 7/2006 |

* cited by examiner

*Primary Examiner* — Olivia C Chang
(74) *Attorney, Agent, or Firm* — Klarquist Sparkman, LLP

(57) ABSTRACT

A bone screw cutting system can include a cutting assembly having a plurality of blades. The system can further include a position adjustment assembly coupled to the cutting assembly and configured to receive a bone screw blank and position the bone screw blank relative to the cutting assembly. The cutting assembly is configured to cut a bone screw blank received by the position adjustment assembly and to form a self-tapping end portion at a cut end of a resulting cut bone screw.

19 Claims, 35 Drawing Sheets

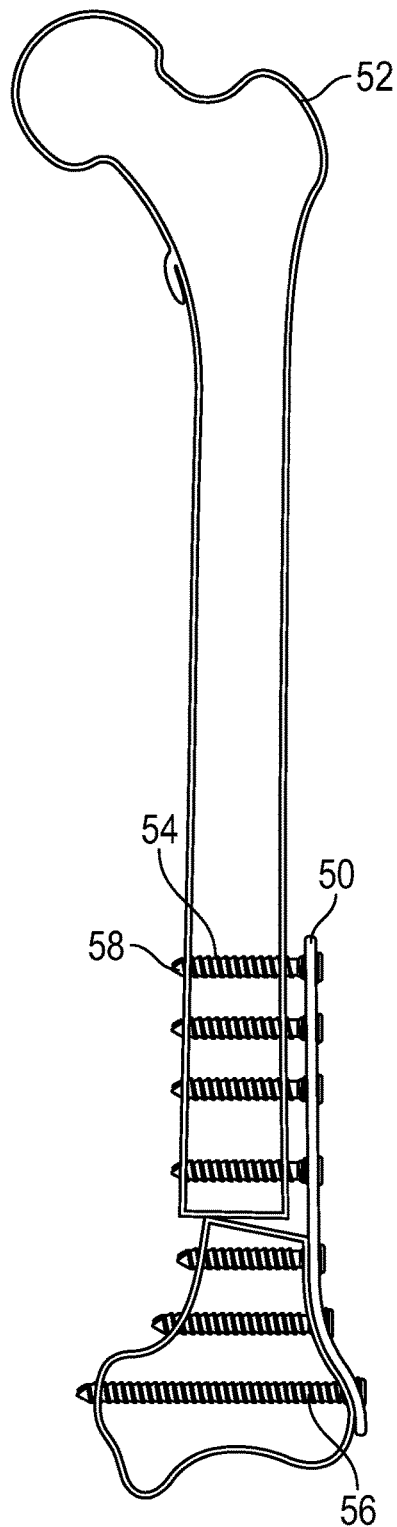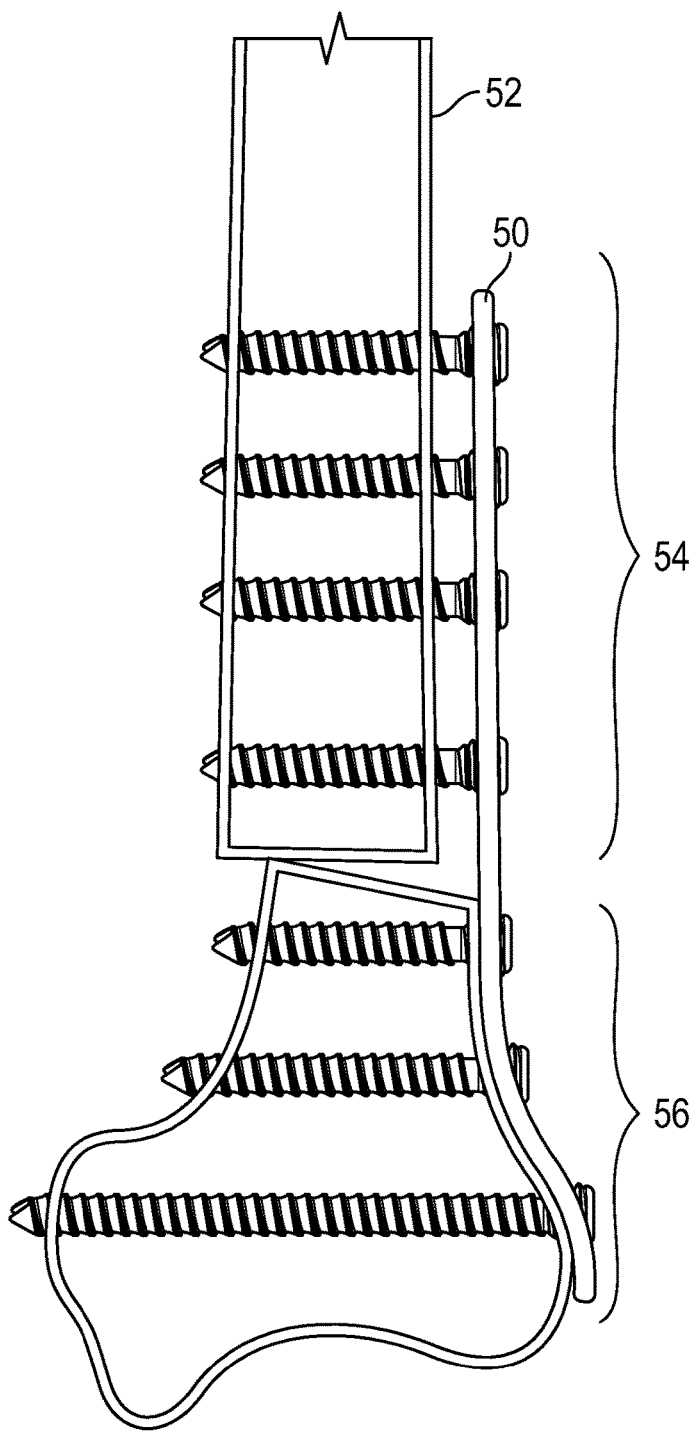
FIG. 4A
FIG. 4B

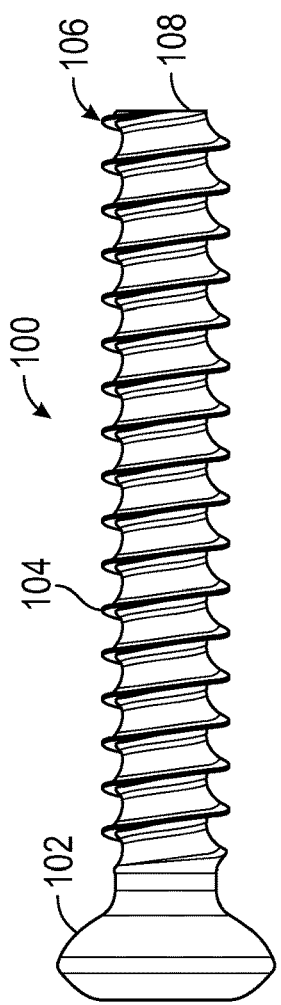
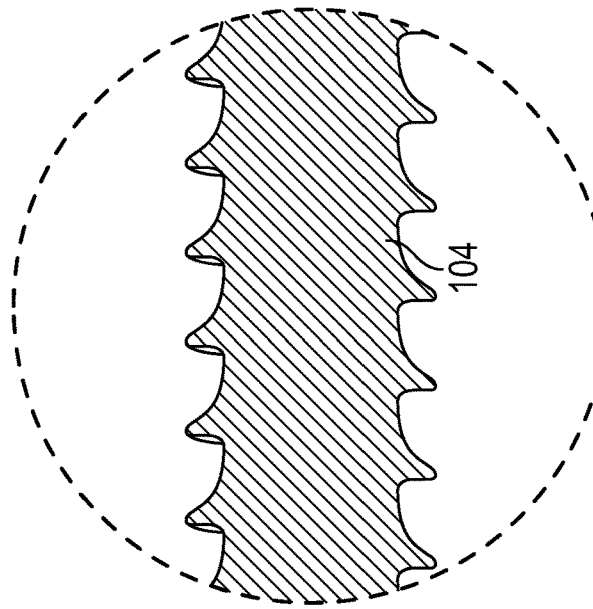
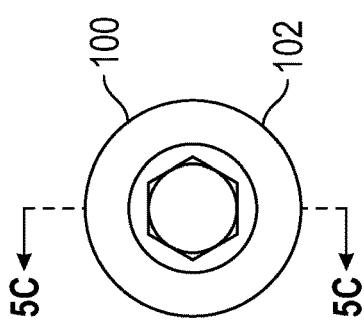
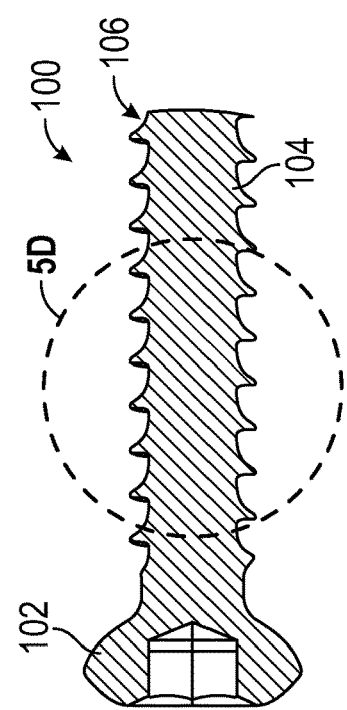
FIG. 5B
FIG. 5D
FIG. 5A
FIG. 5C

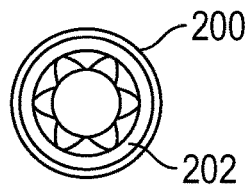
FIG. 6A
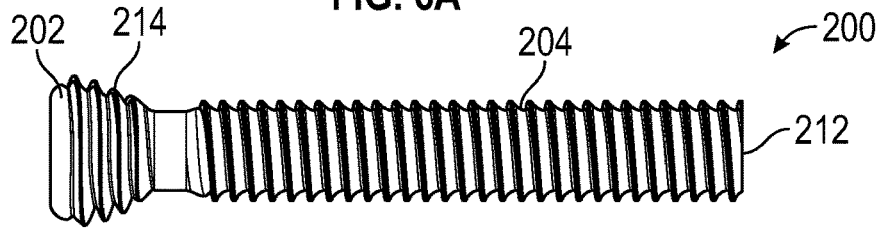
FIG. 6B
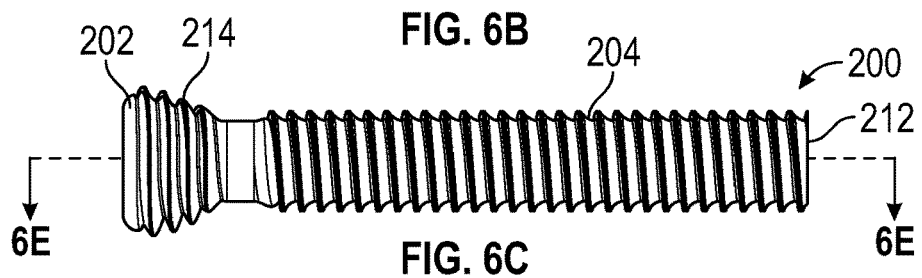
FIG. 6C
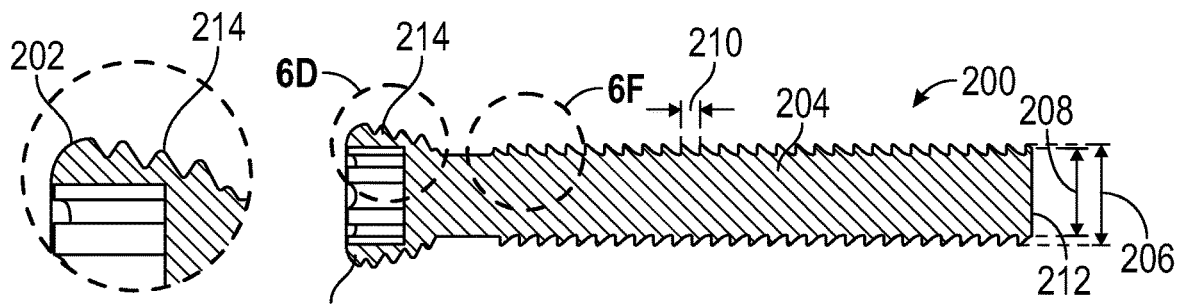
FIG. 6D
FIG. 6E
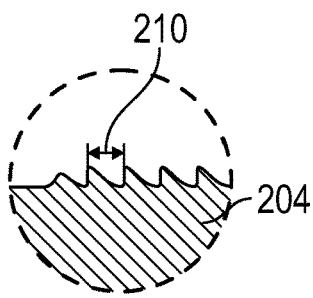
FIG. 6F
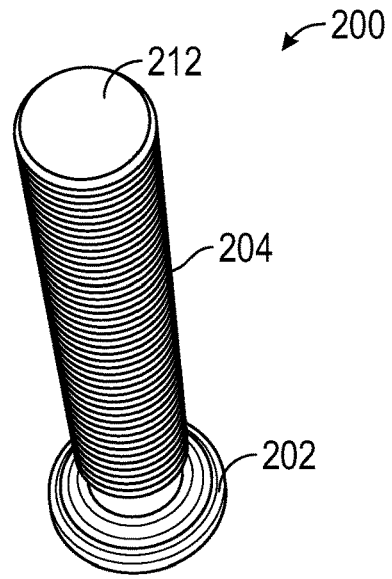
FIG. 6G

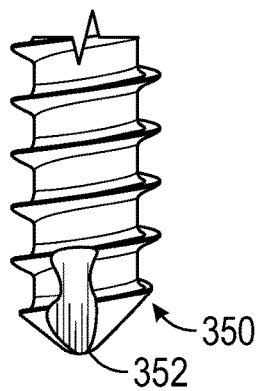 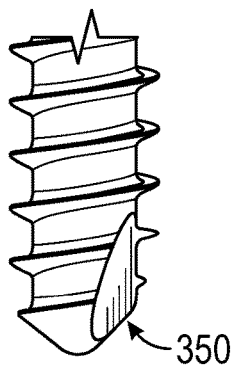 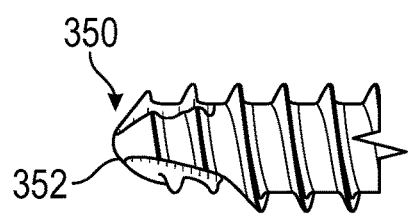
FIG. 12A          FIG. 12B          FIG. 12C
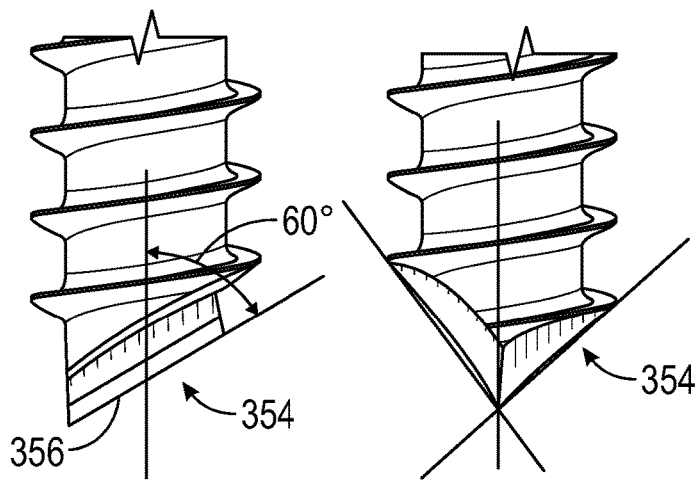 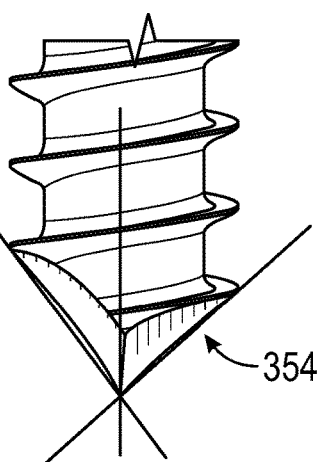 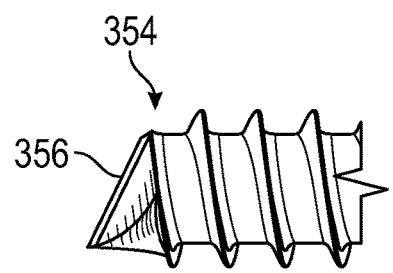
FIG. 12D          FIG. 12E          FIG. 12F
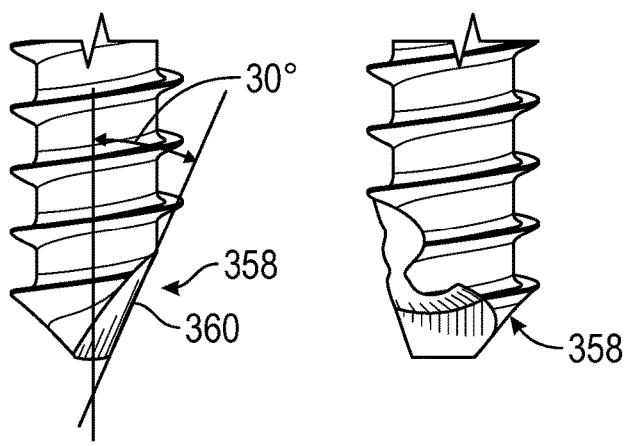 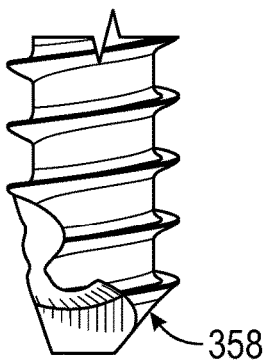 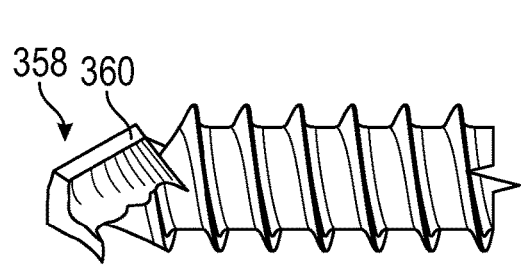
FIG. 12G          FIG. 12H          FIG. 12I

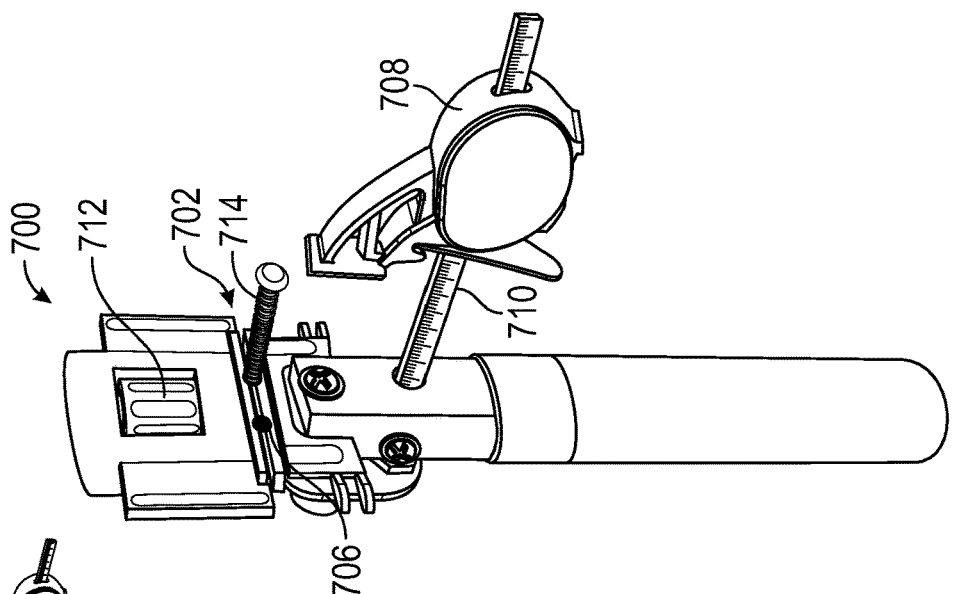
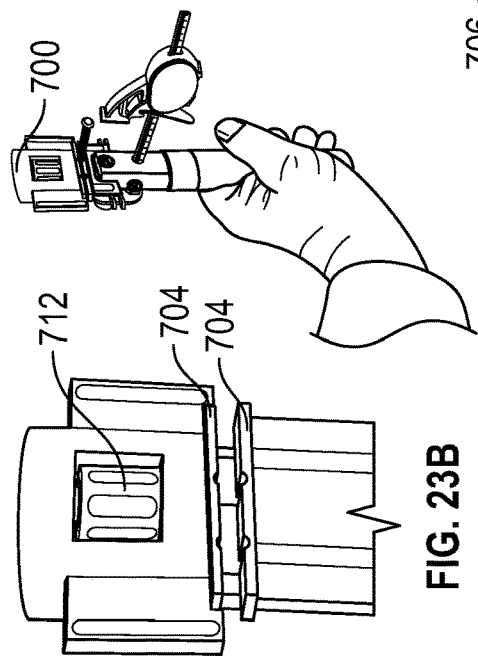
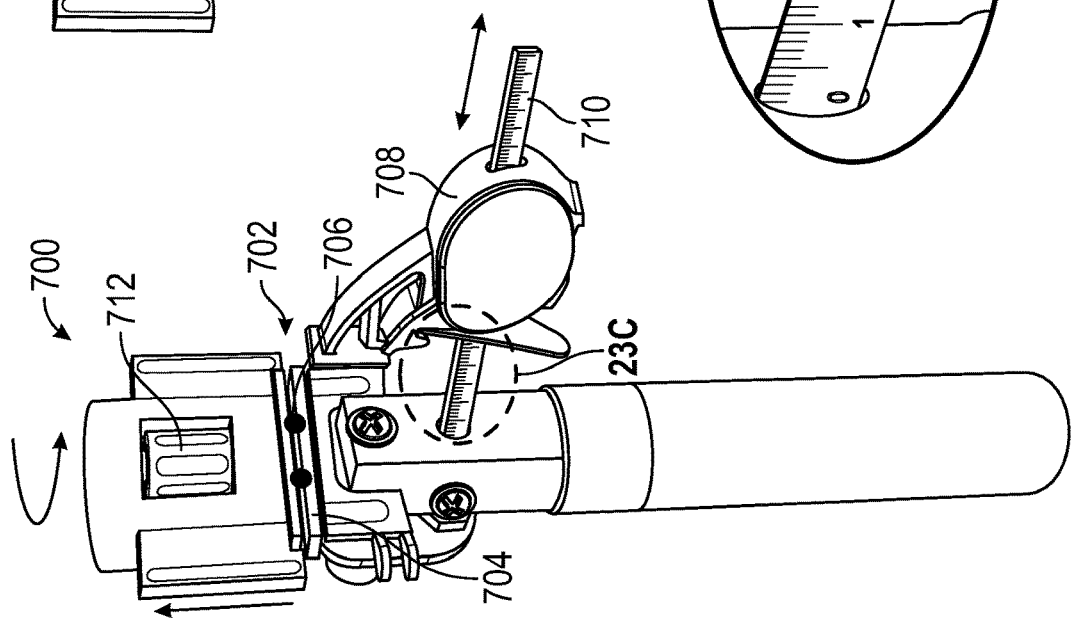
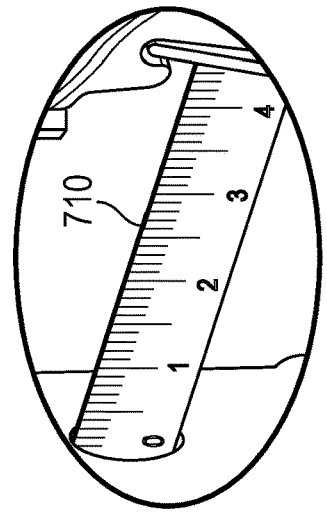
FIG. 23A
FIG. 23B
FIG. 23C
FIG. 23D
FIG. 23E

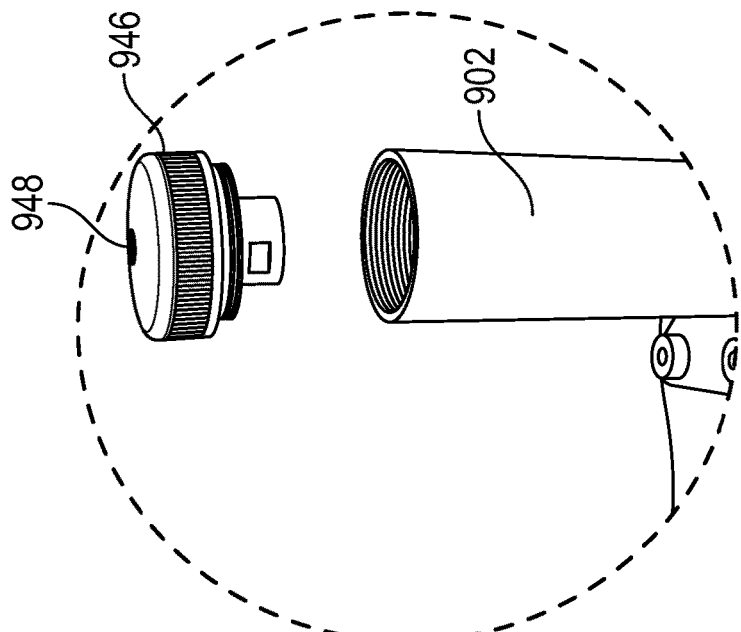
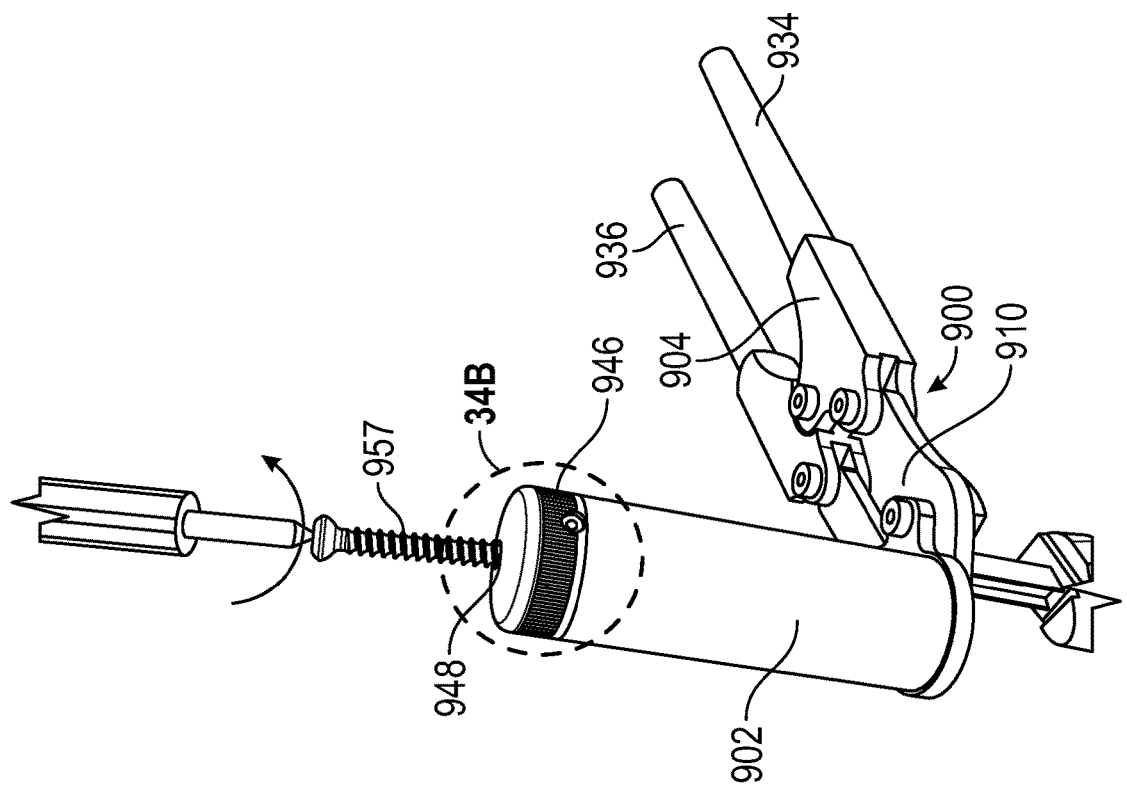
FIG. 34B
FIG. 34A

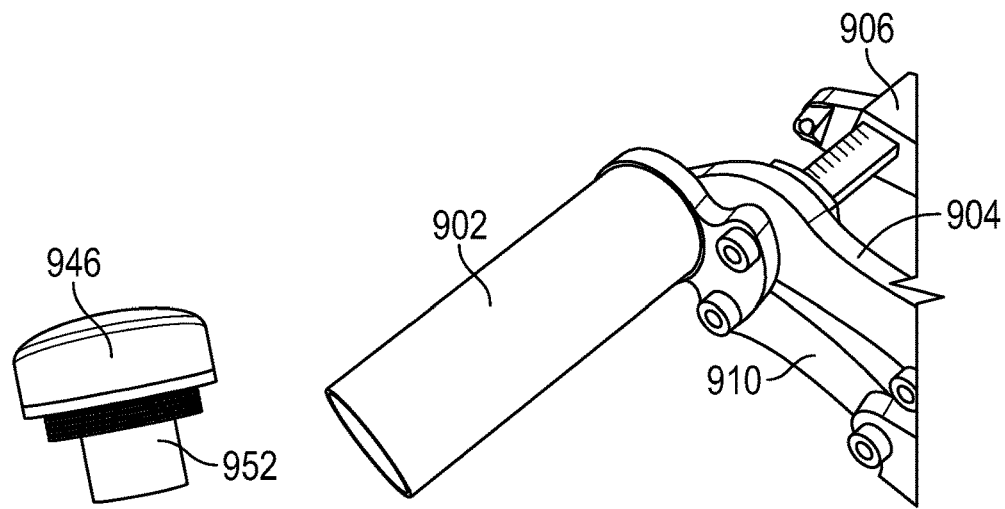
FIG. 41
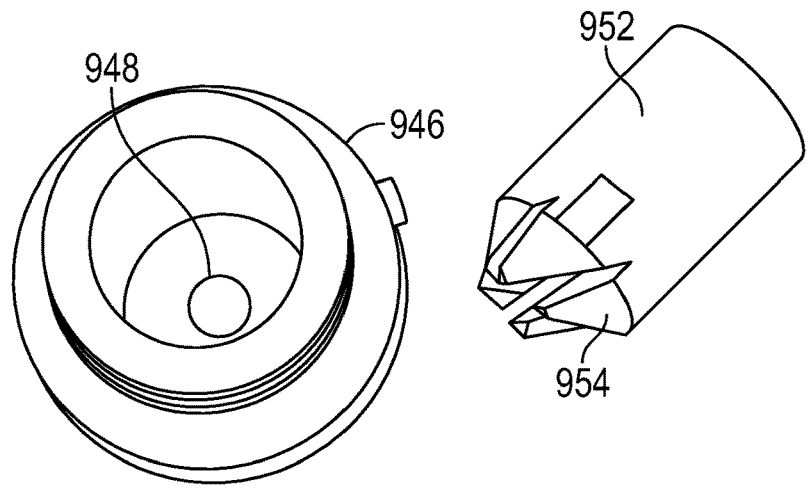
FIG. 42
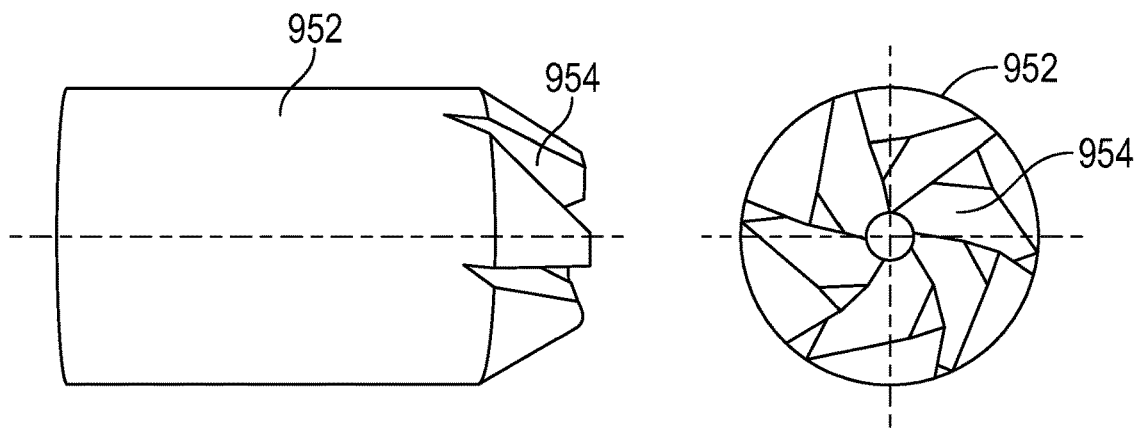
FIG. 43A  FIG. 43B

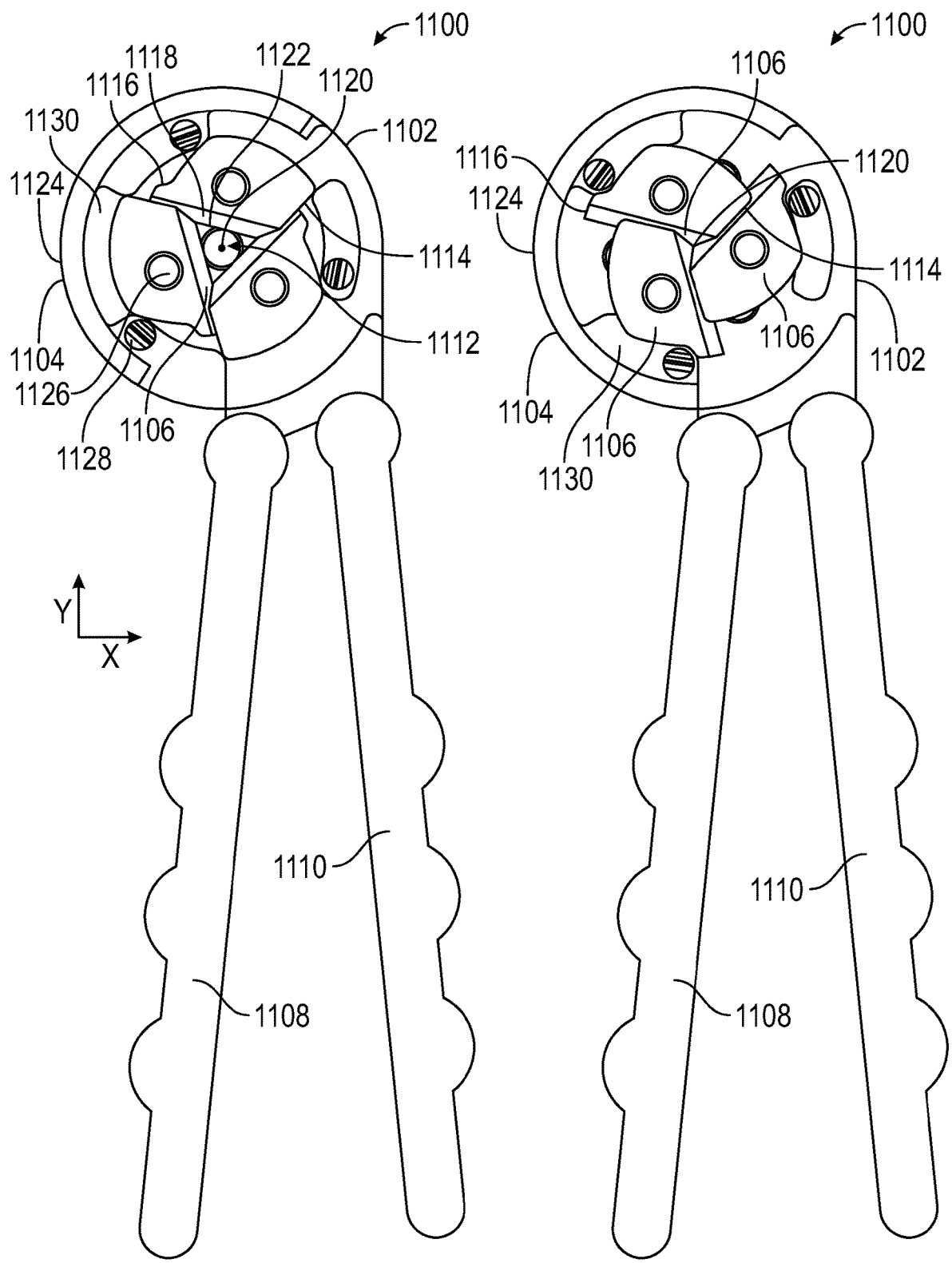
FIG. 50   FIG. 51

SURGICAL BONE SCREW METHOD AND APPARATUS

CROSS REFERENCE TO RELATED APPLICATION

This application claims the benefit of U.S. Provisional Application Ser. No. 62/960,540, filed Jan. 13, 2020, which is incorporated by reference herein.

FIELD

The present disclosure pertains to bone screws for orthopedic surgical procedures, apparatus for forming such screws, and systems and methods of implanting and storing such screws.

BACKGROUND

Orthopedic surgical procedures for repairing various bone fractures or other injuries can utilize a plurality of bone screws to fix a bone plate to the bone. Bone screws are typically provided in two primary categories: cancellous bone screws configured for fixation in the soft, spongy interior or marrow of a bone, and cortical bone screws configured for fixation in the more dense, harder, exterior cortical bone. Existing cortical bone screws are typically configured as one of a cortical bone screw and a cortical locking bone screw, where locking bone screws have threads incorporated into the head of the screw and configured to engage corresponding threads in a bone plate. These screws are typically offered in self-tapping or non-self-tapping configurations. In certain examples, the bone is prepared with a drill guide and a specified drill bit sized for the intended screw. If a non-self-tapping bone screw is used, the drilled pilot hole typically requires tapping to create threads in the bone before the screw can be inserted.

In a typical surgical procedure using bone plates and existing bone screws, as described above, the bone plate and bone screws are typically in a non-sterile condition and must be autoclaved or sterilized at the hospital or clinic before the procedure. Typically, multiple bone plates of the same or different designs, and multiple bone screws of different sizes, shaft lengths, shaft diameters, thread pitches, and/or tip configurations (e.g., self-tapping and non-self-tapping) are sterilized and made available for the surgery to improve intra-operative options. Generally, a selection of cortical bone screws of several sizes and in many different lengths are available for surgery (e.g., on site at the hospital or clinic, or in a mobile surgeon's supply). A similar selection of locking screws in several sizes and in many lengths can also be available. Thus, depending on the type of surgical procedure, between 250 to 500 bone screws or more may need to be sourced, sterilized, and brought into the operating room for a single surgery. For example, each of these screws/implants must be prepared in advance of the surgical procedure and are typically steam autoclaved so that they are available in a sterile condition for the surgery. This imposes a significant burden on the surgeon and/or the hospital in the form of keeping a large inventory of bone screws and implants, gathering or sourcing these materials prior to a surgery, sterilizing them before the procedure (many more than will actually be used in the procedure), and then restocking the unused hardware after the procedure. Accordingly, a need exits for improved systems and/or apparatuses for reducing an amount of hardware needed for a surgical procedure and simplifying the surgery preparation process.

SUMMARY

Disclosed herein are examples of systems, apparatuses, or tools for positioning and cutting a bone screw blank to a specified length and forming a self-tapping end portion on the resulting cut screw. In some embodiments, such systems can comprise a cutting assembly including a plurality of blades configured to cut an end portion of a screw blank and form a self-tapping end portion. In some embodiments, the systems can further comprise a position adjustment assembly coupled to the cutting assembly and configured to position a portion of the position adjustment assembly configured to hold or receive the screw blank relative to the cutting assembly, thereby resulting in cutting the screw blank to the specified length.

In one representative embodiment, a bone screw cutting system comprises: a cutting assembly comprising a plurality of blades; and a position adjustment assembly coupled to the cutting assembly and configured to receive a bone screw blank and position the bone screw blank relative to the cutting assembly. The cutting assembly is configured to cut a bone screw blank received by the position adjustment assembly and to form a self-tapping end portion at a cut end of a resulting cut bone screw.

In some embodiments, the position adjustment assembly includes a mounting member and a measurement member, the mounting member configured to slide along a length of the measurement member, relative to the cutting assembly, and receive an end portion of the bone screw blank that is arranged opposite an end portion of the bone screw blank to be cut by the cutting assembly.

In some embodiments, the system further comprises a container portion configured to receive severed portions of bone screw blanks cut with the cutting assembly.

In some embodiments, the position adjustment assembly is coupled to a first side of the cutting assembly and the container portion is coupled to a second side of the cutting assembly, opposite the first side.

In some embodiments, the container portion includes a first end coupled to the second side of the cutting assembly and a cap including a deburring member is removably coupled to a second end of the container portion. The deburring member is configured to hone the self-taping end portion of the resulting cut bone screw.

In some embodiments, the position adjustment assembly is coupled to a first side of the cutting assembly. The system further comprises a receptacle coupled to a second side of the cutting assembly, the second side opposite to the first side. A die cartridge including a threaded portion is disposed within the receptacle, with the threaded portion disposed adjacent the plurality of blades of the cutting assembly, the threaded portion configured to reform threads at the cut end of the resulting cut bone screw to further form the self-tapping end portion.

In some embodiments, the plurality of blades includes at least three blades arranged in a plane defined by a cutting head of the cutting assembly, the at least three blades configured to move from an open position to a closed position. In the open position a central gap is defined between the three blades and in the closed position the blades converge such that the gap is closed such that an end portion of the bone screw blank received in the central gap is cut into an at least three-sided cutting point that forms the self-tapping end portion.

In some embodiments, each blade of the at least three blades includes a first sliding surface disposed between a first end and second end of the blade, the first and second ends disposed opposite one another. The first sliding surface includes a cutting edge configured to cut the end portion of the bone screw blank.

In some embodiments, the first sliding surface is configured to slide along the first end of an adjacent blade of the at least three blades when moving from the open position to the closed position. In the closed position the second end of each blade is disposed closer to an outer perimeter of the cutting head than when in the open position.

In some embodiments, the cutting assembly further comprises two opposing handles coupled to a gear system of the cutting head and configured to actuate the plurality of blades to move from the open position to the closed position via an outer gear coupled to each blade of the plurality of blades.

In some embodiments, the cutting assembly further comprises two opposing handles coupled to a rotatable plate of the cutting head and configured to actuate the plurality of blades to move from the open position to the closed position.

In some embodiments, the cutting assembly further comprises two opposing handles coupled to the plurality of blades and configured to actuate the plurality of blades to cut the bone screw blank.

In some embodiments, the blades of the cutting assembly comprise radiused edges.

In some embodiments, the blades of the cutting assembly are tapered to fit between threads of the bone screw blank.

In another representative embodiment, a bone screw cutting system comprises: a cutting assembly comprising a plurality of blades configured to converge toward one another in a same plane from an open position to a closed position, wherein in the open position a central opening is formed between the plurality of blades and in the closed position the central opening is closed. The system further comprises a position adjustment assembly configured to receive a bone screw blank and position the bone screw blank relative to the cutting assembly. The cutting assembly is configured to cut a bone screw blank received by the position adjustment assembly and to form an at least three-sided cutting point at a cut end of the resulting cut bone screw.

In some embodiments, the at least three-sided cutting point is configured to be self-tapping and self-form threads inside a drilled hole.

In some embodiments, each blade of the plurality of blades includes a first sliding surface disposed between a first end and second end of the blade, the first and second ends disposed opposite one another, and the first sliding surface includes a cutting edge configured to cut the bone screw blank and form one side of the at least three-sided cutting point.

In some embodiments, the first sliding surface is configured to slide along the first end of an adjacent blade of the plurality of blades when moving from the open position to the closed position. In the closed position the second ends of each blade is disposed closer to an outer perimeter of the cutting head than when in the open position.

In another representative embodiment, a bone screw cutting system comprises: a cutting assembly comprising at least three blades arranged in a circle on a cutting head of the cutting assembly, the at least three blades movable between an open position where a central aperture is formed between the plurality of blades, the central aperture configured to receive a first end portion of a bone screw blank, and a closed position where the central aperture is closed by the at least three blades. The cutting assembly is configured to cut the first end portion of the bone screw blank received within the central aperture and to form an at least three-sided cutting point at the cut, first end portion of the resulting cut bone screw.

In some embodiments, the system further comprises a position adjustment assembly configured to receive a second end portion of the bone screw blank and position the bone screw blank relative to the cutting assembly, the second end portion disposed opposite the first end portion.

In some embodiments, each blade of the at least three blades includes a sliding surface with a cutting edge disposed between a first end and a second end of the blade. In the closed position first ends of the blades converge together to close the central aperture and second ends of the blades are disposed closer to a perimeter of the cutting head than when in the open position.

The foregoing and other objects, features, and advantages of the disclosed technology will become more apparent from the following detailed description, which proceeds with reference to the accompanying figures.

BRIEF DESCRIPTION OF THE DRAWINGS

FIG. 4A illustrates a bone plate secured to a bone with a small portion of the tips of the bone screws extending from the bone on the opposite side of the bone from the bone plate.

FIG. 4B is a detail view of the bone of FIG. 4A illustrating the arrangement of the bone plate and bone screws to the bone in more detail.

FIGS. 5A-5D illustrate various views of a cortical screw blank, according to one embodiment.

FIGS. 6A-6G illustrate various views of a locking screw blank, according to one embodiment.

FIGS. 12A-12C illustrate various rotational side views of a self-tapping end portion with a 90° edge that can be formed on a bone screw blank using the systems and methods described herein.

FIGS. 12D-12F illustrate various rotational side views of a self-tapping end portion with a 60° edge that can be formed on a bone screw blank using the systems and methods described herein.

FIGS. 12G-12I illustrate various rotational side views of a self-tapping end portion with a 30° edge that can be formed on a bone screw blank using the systems and methods described herein.

FIGS. 23A-23E illustrate another embodiment of a system for positioning and cutting a bone screw blank to a specified length and forming a self-tapping end portion on the screw blank.

FIG. 34A illustrates a container portion of the system of FIG. 28 and a process for honing the self-tapping end portion of the cut screw after cutting.

FIG. 34B is a magnified view of a cap configured to couple to the container portion of FIG. 34A, the cap including a deburring member.

FIG. 41 is a perspective view of a container portion of the system of FIG. 29 with a cap of the container portion removed and with a deburring member coupled to the cap.

FIG. 42 illustrates the deburring member separated from the cap of FIG. 41.

FIG. 43A is a side view of the deburring member of FIGS. 41 and 42.

FIG. 43B is an end view of the deburring member of FIGS. 41 and 42.

FIG. 50 is a plan view of another embodiment of a system for positioning and/or cutting a bone screw blank to a specified length and forming a self-tapping end portion on the resulting cut screw, illustrating a cutting assembly of the system in an open position.

FIG. 51 is a plan view of the system of FIG. 50, illustrating the cutting assembly in a closed position.

DETAILED DESCRIPTION

Figure 1A:
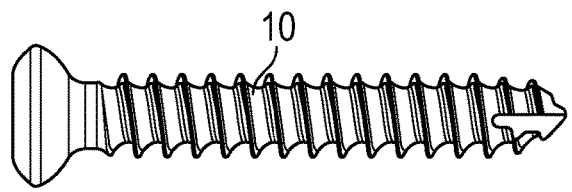
FIGS. 1A-2D illustrate various embodiments of bone screws.
Figure 1B:
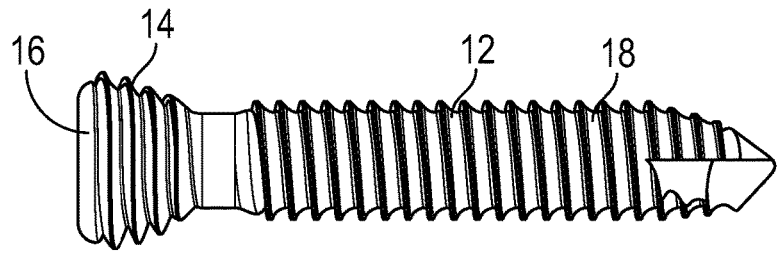

The present disclosure pertains to bone screws for orthopedic surgical procedures, and systems and methods of cutting and shaping bone screw blanks to a specified length intraoperatively. Bone screws are typically provided in two primary categories: cancellous bone screws configured for fixation in the soft, spongy interior or marrow of a bone, and cortical bone screws configured for fixation in the more dense, harder, exterior cortical bone. Existing cortical bone screws are typically configured as one of a cortical bone screw and a cortical locking bone screw. FIG. 1A illustrates a representative example of a cortical bone screw 10 and FIG. 1B illustrates a representative example of a cortical locking bone screw 12. The cortical locking bone screw 12 can have threads 14 incorporated into the head 16 of the bone screw and 12 configured to engage corresponding threads in a bone plate (e.g., bone plate 40 shown in FIG. 3) in addition to engaging the hard cortical bone with the body, shaft, or shank 18 of the bone screw 12.

Figure 2A:
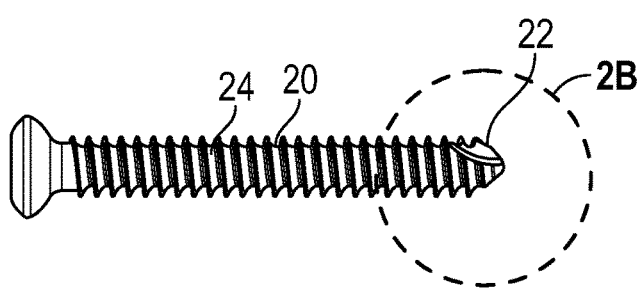
Figure 2B:
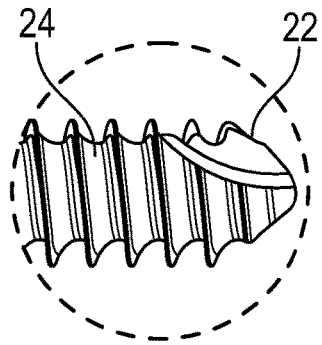
Figure 2C:
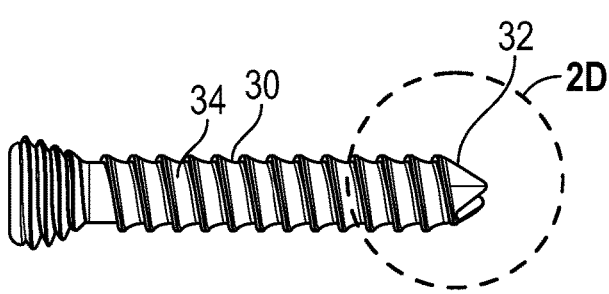
Figure 2D:
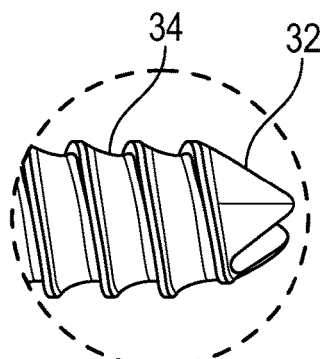

These bone screws are typically offered in self-tapping or non-self-tapping configurations. FIGS. 2A and 2B illustrate a representative embodiment of a self-tapping cortical bone screw 20 having a body 24 with a self-tapping end 22 (as shown in the detail view of FIG. 2B). FIGS. 2C and 2D illustrate a representative embodiment of a non-self-tapping cortical locking bone screw 30 having an end 32 in a body 34 of the bone screw 30 that is not self-tapping (as shown in the detail view of FIG. 2D). In certain examples, the bone is prepared with a drill guide and a specified drill bit sized for the intended bone screw. If a non-self-tapping bone screw (e.g., bone screw 30 in FIGS. 2C and 2D) is used, the drilled pilot hole typically requires tapping to create threads in the bone before the bone screw can be inserted.

In a typical surgical procedure using bone plates and existing bone screws, as described above, the plate and screws are typically in a non-sterile condition and must be autoclaved or sterilized at the hospital or clinic before the procedure. Typically, multiple plates of the same or different designs, and multiple screws of different sizes, shaft lengths, shaft diameters, thread pitches, and/or tip configurations (e.g., self-tapping and non-self-tapping) are sterilized and made available for the surgery to improve intra-operative options. Generally, a selection of cortical bone screws of several sizes and in 45 different lengths, or more, are available for surgery (e.g., on site at the hospital or clinic, or in a mobile surgeon's supply. A similar selection of locking bone screws in several sizes and in 45 lengths are also available. Bone screws of both types are also kept available in quantities of six for each size and length. Thus, depending on the type of surgical procedure, between 250 to 500 bone screws or more need to be sourced, sterilized, and brought into the operating room for a single surgery. For example, each of these screws/implants must be prepared in advance of the surgical procedure and are typically steam autoclaved so that they are available in a sterile condition for the surgery. This imposes a significant burden on the surgeon and/or the hospital in the form of keeping a large inventory of screws and implants, gathering or sourcing these materials prior to a surgery, sterilizing them before the procedure (many more than will actually be used in the procedure), and then restocking the unused hardware after the procedure.

The systems, apparatus, and methods described herein can alleviate this burden by providing bone screws of uniform size, referred to herein as bone screw blanks, which can be cut to a specified length in the operating room using a positioner/cutter apparatus (which can also be referred to as a shearing tool or apparatus). The described apparatuses can also form self-tapping end portions on the bone screw blanks intraoperatively after they are cut to a specified length. Bone screw blanks that have been cut and/or finished using the systems described herein are referred to as "cut" or "finished" bone screws. Embodiments of pre-sterilized kits including orthopedic implants and a plurality of bone screw blanks corresponding to the number of bone screws typically required for a specific procedure are also provided.

As used herein, "self-tapping" screws or a "self-tapping" end portion of a screw refers to a finished tip of a screw that is configured to produce a thread in a hole or bore (in a material, such as bone) into which it is driven. In this way, a self-tapping bone screw or a bone screw that includes a self-tapping end portion can be secured into a hole or bore without having to first tap the hole or bore. For example, in thin cortical bone and/or dense cancellous bone, a self-tapping bone screw or bone screw including a self-tapping end portion can self-form threads in a hole or bore in the bone.

The following examples are provided with reference to veterinary orthopedic surgical procedures such as the tibial plateau leveling osteotomy (TPLO), for purposes of illustration. However, the bone screws, screw forming and fixation systems, and methods described herein are not limited to veterinary applications or TPLO procedures, and are also applicable to orthopedic surgical procedures in humans.

Figure 3:
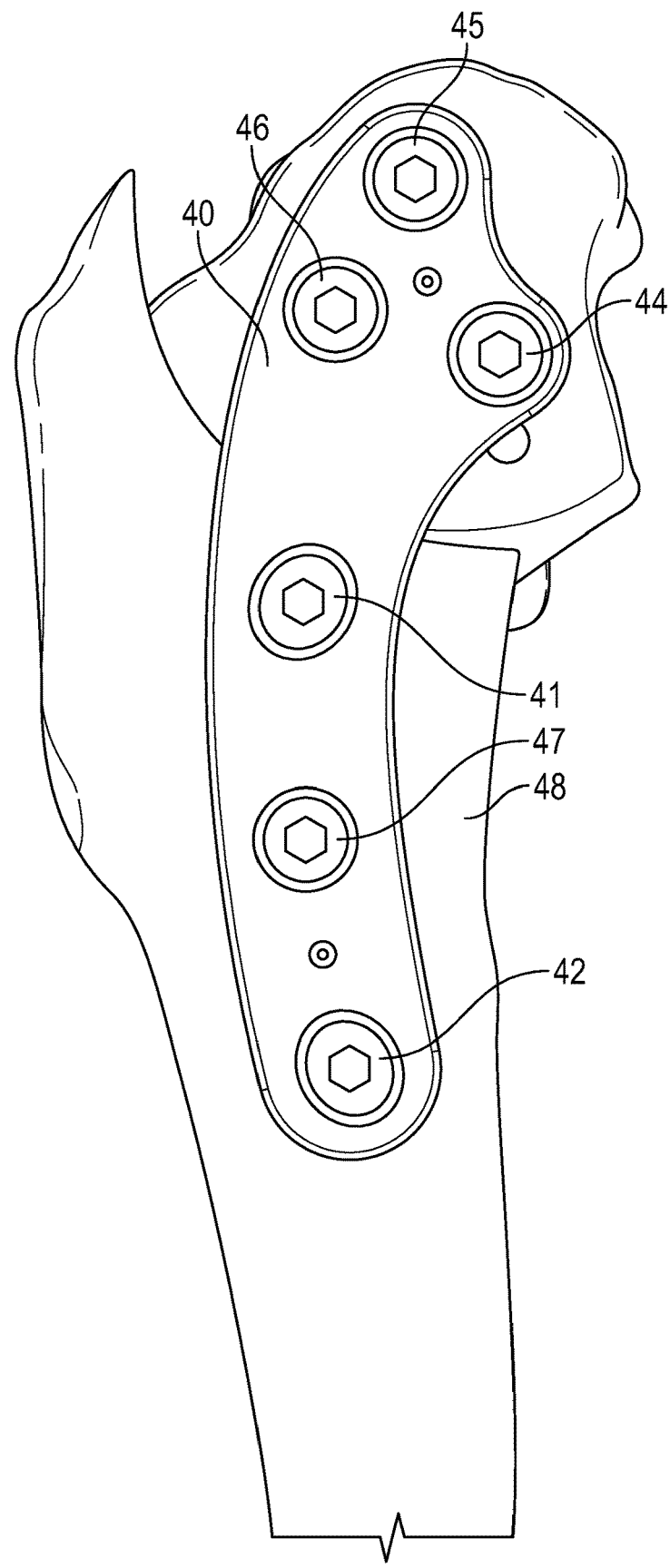
FIG. 3 illustrates a tibial plateau level osteotomy bone plate, according to one embodiment.

Bone plates for specific surgical procedures (including pancarpal arthrodesis, pantarsal arthrodesis, triple pelvic osteotomy, TPLO, hock (ankle) fusion and/or various bone fractures) require different length bone screws in both cortical and locking designs, which can depend on the geometry of the bone. For example, in veterinary applications, a typical surgical procedure for a TPLO can begin with radiographs of the patient's leg(s). The radiographs are then analyzed to determine the appropriate size of the osteotomy plate. The plate, along with approximately 280 bone screws, must then be autoclaved and brought into the operating room for the surgery. For example, for a typical canine patient (e.g., a Golden Retriever weighing 66 lbs (30 kg)), a 3.5 mm TPLO plate may be appropriate. A representative example of a TPLO plate 40 is illustrated in FIG. 3 and described in greater detail in U.S. Pat. No. 10,226,288, which is incorporated herein by reference. In a typical procedure, six (6) bone screws can be used to secure the plate to the bone 48, namely two (2) 3.5 mm diameter cortical bone screws 41 and 42, and four (4) 3.5 mm diameter locking bone screws 44-47. The type of bone screw and the average length of the bone screw typically used for the canine patient noted above, for each bone screw hole in FIG. 3, can include a 22 mm length cortical bone screw 41, a 24 mm length cortical bone screw 42, a 32 mm length locking bone screw 44, a 38 mm length locking bone screw 45, a 30 mm length locking bone screw 46, and a 22 mm length locking bone screw 47.

The type of bone screw and the length are typically determined during the procedure (e.g., after drilling holes at the specified locations in the bone and measuring the depth).

Typically, bone screws are selected having lengths such that 1 mm to 3 mm of the screw tip will extend beyond the bone surface on the opposite side of the bone from the plate when the bone screw is inserted into the opening. For example, as illustrated in FIGS. 4A and 4B, an exemplary distal femoral osteometry is shown including a bone plate 50 coupled to a bone 52 (e.g., femur) with a plurality of locking bone screws 54 and cortical bone screws 56. As shown in FIG. 4A, the lengths of the bone screws can be chosen such that the tip 58 of each bone screw does not extend too far past the cortex of the bone 52. For example, as shown in FIG. 4B, the distal-most cortical bone screw 56 is longer than the rest of the bone screws due to its positioning in a wider portion of the bone 52.

The apparatus, systems, and methods described herein provide a way to reduce the bone screw inventory required for a specified orthopedic procedure (human or veterinary) by using bone screw blanks, which can be cut to a desired length intraoperatively using one of various hand tool embodiments described herein. Such systems and methods can provide the ability to create surgical kits for specific bone fractures and orthopedic procedures. Each kit can include one or more bone plates of specified design and size, along with a series of bone screw blanks which can be cut to a specified length during the surgery. The bone screw blanks can correspond to the types and sizes typically required for the specified procedure and the associated implant. Such kits can be provided in a cleaned and pre-sterilized condition, eliminating the need for autoclaving the bone screws and implants at the hospital, and reducing the potential for delays and increased anesthesia duration resulting from a lack of appropriately prepared hardware during a procedure.

First Representative Embodiment

FIGS. 5A-5D illustrate different views of a representative example of a cortical bone screw blank 100, according to one embodiment. For example, an end view (FIG. 5A), side view (FIG. 5B), cross-sectional side view (FIG. 5C), and a magnified, cross-sectional side view of a portion of the bone screw blank 100 (FIG. 5D) are shown. The bone screw blank 100 can comprise a head 102 and a threaded shank or shaft 104 having specified major and minor diameters, and a specified thread pitch. The bone screw blank shaft 104 can include an end portion 106 having a flat end or surface 108.

FIGS. 6A-6G illustrate different views of a representative example of a locking bone screw blank 200, according to one embodiment. The bone screw blank 200 can comprise a head 202, a shank 204, specified major diameter 206 and minor diameter 208 (FIG. 6E), thread pitch 210, and a flat end portion 212 similar to the bone screw blank 100. Additionally, the head 202 of the bone screw blank 200 can comprise threads 214 configured to engage corresponding threads in a bone plate or other implant to engage or lock the bone screw to the bone plate. Additional embodiments of locking bone screws are described in U.S. Pat. No. 8,696,715, which is incorporated herein by reference.

The cortical bone screw blanks and/or the locking bone screw blanks can be provided in one more lengths. For example, in certain embodiments the cortical bone screw blanks and the locking bone screw blanks can each be available in lengths of 40 mm and 60 mm, although the bone screw blanks can be provided in any length and any number of different lengths depending upon the particular procedure.

Figure 7:
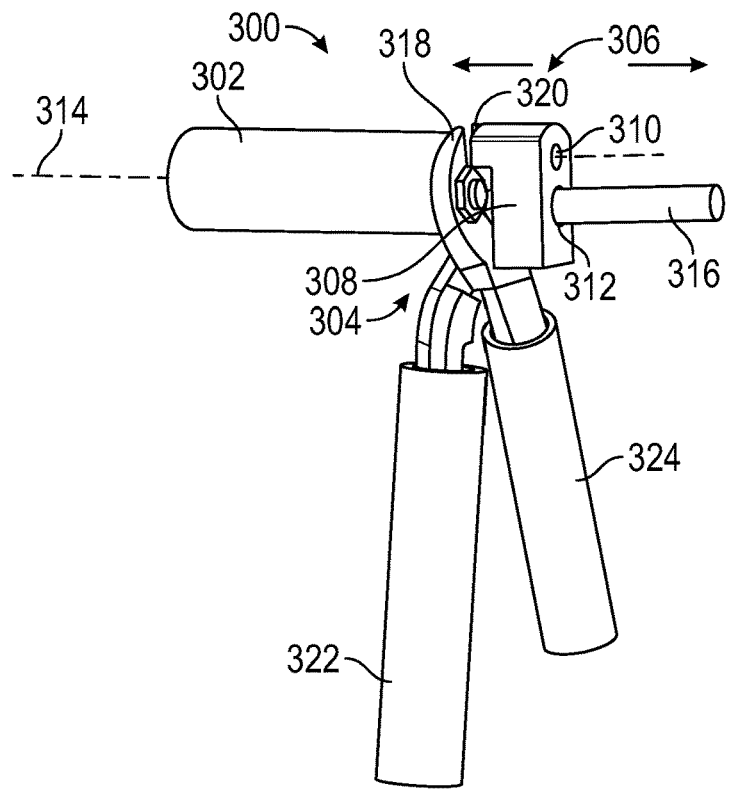
FIG. 7 is a first perspective view of a system for positioning and cutting a bone screw blank to a specified length, and forming a self-tapping end portion thereon, according to one embodiment.

FIG. 7 illustrates a representative example of a system/apparatus/tool 300 configured to position a bone screw blank (e.g., one of the bone screw blank 100 or bone screw blank 200), cut the bone screw blank to a specified length, and form a self-tapping end portion on the bone screw blank, according to one embodiment. The apparatus 300 can comprise a container 302, a cutting tool 304, and a position adjustment assembly 306 coupled together. The position adjustment assembly 306 can include a housing or mounting member 308 comprising an opening 310 and an opening 312. The opening 310 can be oriented along an axis 314 and can be configured to receive a bone screw blank to be cut by the apparatus. The mounting member 308 can be disposed on a cylindrical member 316 extending through the opening 312 and can be movable or translatable along the member 316.

The cutting tool 304 can comprise a pair of opposed jaws/cutting edges/blades 318 and 320 coupled to respective members configured as handles 322 and 324. Pivoting the handles 322 and 324 together (e.g., toward one another) can bring the blades 318 and 320 together in the manner of shears, scissors, snips, diagonal cutters, diagonal pliers, wire cutters, or bolt cutters.

Figure 8:
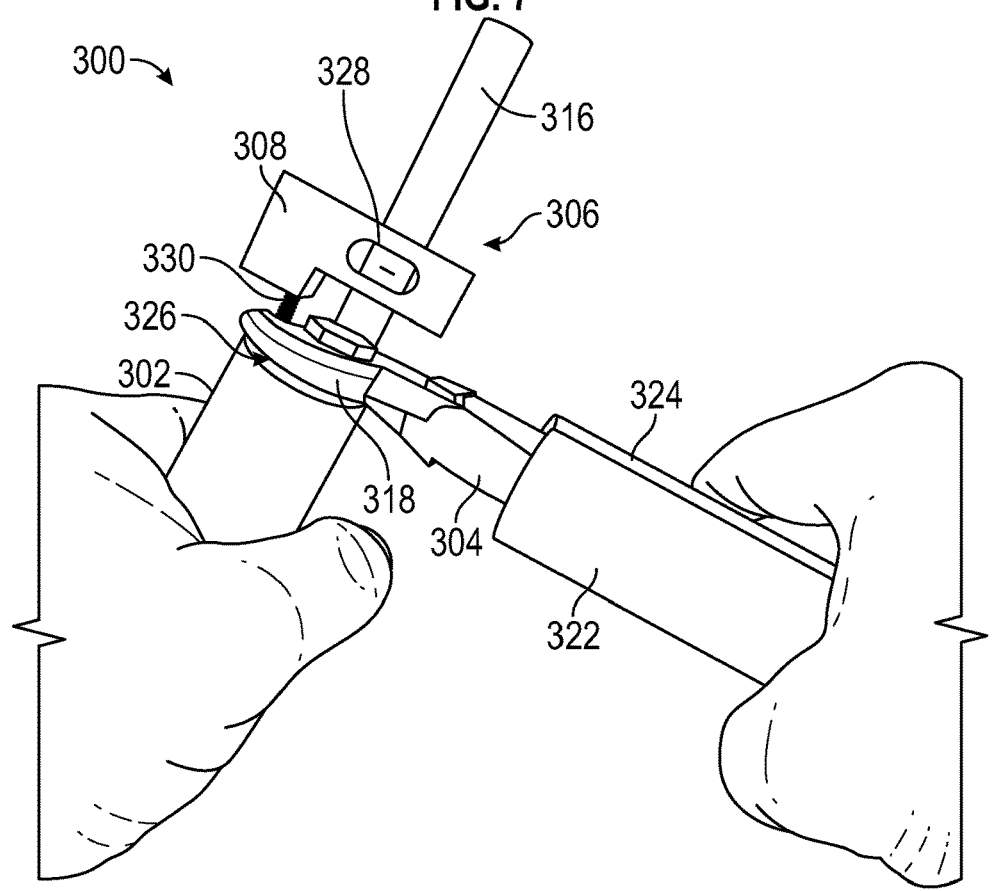
FIG. 8 is a second perspective view of the system of FIG. 7.

Referring to FIG. 8, the container 302 can comprise an opening 326 oriented toward the mounting member 308. The mounting member 308 can also comprise an opening, window, or viewport 328 through which a length scale on the cylindrical member 316 can be viewed.

In certain embodiments, the opening 310 (FIG. 7) can be threaded to receive and retain a bone screw blank to be cut. In certain embodiments, the apparatus can comprise multiple mounting members 308 comprising openings with different thread pitches and/or diameters to accommodate corresponding bone screws. In certain embodiments, the mounting member 308 can comprise multiple openings such as the opening 310 comprising different thread pitches and/or diameters (e.g., 3.5 mm, 2.7 mm, 2 mm, or any other diameter).

Still referring to FIG. 8, during a surgical procedure, once an appropriate screw length is determined (e.g., by inserting a depth gauge into a hole drilled in the bone), the surgeon or a technician can select a bone screw blank 330 of the appropriate type and size. The bone screw blank 330 can be inserted into the opening 310 in the mounting member 308. The mounting member 308 can then be moved along the cylindrical member 316 to a distance corresponding to the desired length of the cut bone screw. In certain embodiments, the bone screw and/or the mounting member 308 can be moved along the cylindrical member 316 by turning the bone screw blank. The user can then operate the cutting tool 304 (e.g., by squeezing the handles 322 and 324 together) such that the bone screw blank is cut by the blades 318 and 320. The severed portion of the bone screw blank can then be received in the container 302. As shown in FIG. 8, the container 302 can also be configured as a handle for the user to grip with one hand while operating the cutting tool with the other hand.

Figure 9:
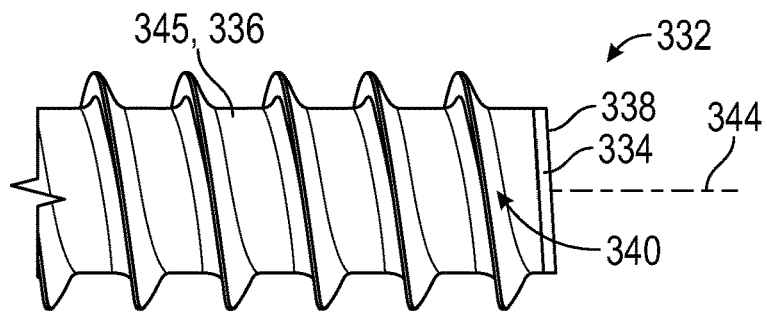
FIG. 9 is a first side view of a self-tapping end portion formed on a bone screw blank, according to one embodiment.
Figure 10:
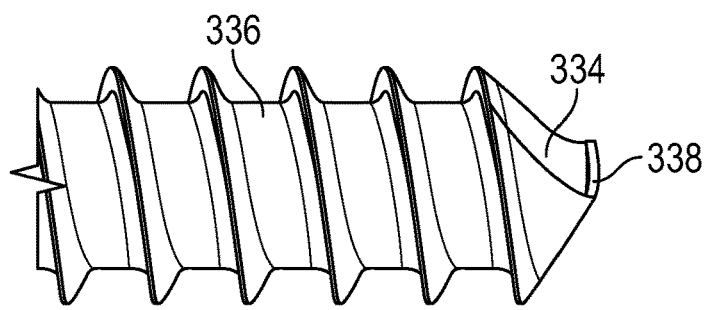
FIG. 10 is a second side view of the self-tapping end portion of FIG. 9 rotated about the longitudinal axis by 90°.
Figure 11:
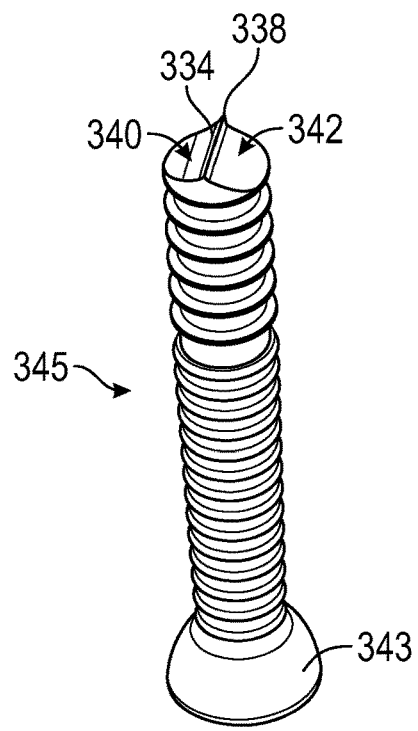
FIG. 11 is a perspective view of a bone screw blank with the self-tapping end portion of FIG. 9.

The cutting tool 304 can be configured to create a self-tapping tip or end portion on the bone screw blank as the bone screw blank is cut by the cutting tool. FIGS. 9-11 illustrate representative examples of a self-tapping end portion that can be created on the resulting cut bone screw 331 using the apparatus 300. In certain embodiments, the cut end portion 332 of the cut bone screw 345 can comprise a tapered, ramped, or wedge-shaped portion 334 (FIGS. 9 and 11). The wedge-shaped portion 334 can extend across the diameter of the shaft 336 (e.g., the minor diameter of the shaft excluding the threads) and can terminate at a straight or substantially straight edge 338. Referring to FIG. 11, the wedge-shaped portion 334 can comprise a first surface 340 and a second surface 342 on opposite sides of the edge 338. The first and second surfaces 340 and 342 can be angled toward each other in a direction away from the head portion 343 (FIG. 11) of the cut bone screw 345 along a longitudinal axis 344 (FIG. 9) of the bone screw. The edge 338 can also extend across the diameter of the shaft 336. In the illustrated embodiment, the edge 338 can be perpendicular, or substantially perpendicular, to the longitudinal axis 344 of the bone screw, although in other embodiments the edge 338 can be angled relative to the longitudinal axis, such as by 10° to 90° or 30° to 60° depending upon the particular performance characteristics desired. Examples of wedge-shaped portions with angled edges are shown in FIGS. 12 and 13.

Figure 13A:
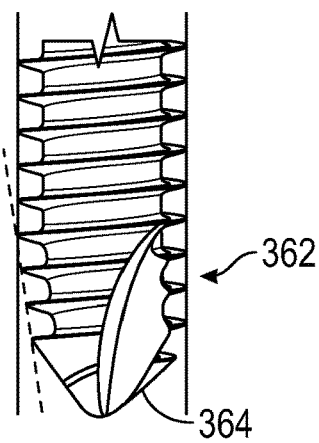
FIGS. 13A and 13B illustrate various rotational side views of another embodiment of a self-tapping end portion that can be formed on a bone screw blank using the systems and methods described herein.
Figure 13B:
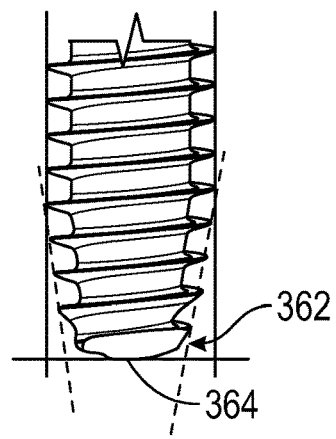

For example, FIGS. 12A-12C show different rotational views of a self-tapping cut end portion 350 with a 90° (e.g., perpendicular) edge 352 measured relative to the longitudinal axis of the bone screw. The bone screws in FIGS. 12A-12C includes three flutes or recesses cut into the end portion of the bone screw, exposing the edges of the threads to facilitate cutting or tapping of threads in bone when the bone screws are driven into bone. In one example, bone screws configured according to the embodiment shown in FIGS. 12A-12C were used as a control in evaluation of the cutting tools and cut bone screws described herein. FIGS. 12D-12F show different rotational views of a self-tapping cut end portion 354 with a 60° edge 356 measured relative to the longitudinal axis of the bone screw. FIGS. 12G-12I show different rotational views of a self-tapping cut end portion 358 with a 30° edge 360. FIGS. 13A and 13B show different rotational views of a self-tapping cut end portion 362 of a locking bone screw with a 90° edge 364 and a tapered or shaved tip or end portion relative to the shaft of the bone screw (as shown by the lines in FIGS. 13A and 13B).

In certain embodiments, the largest dimension of the wedge-shaped portion 334 can be the same or less than the diameter of the shaft 336. For example, the length dimension of the edge 338 (measured diametrically across the shaft of the bone screw) can be the same or smaller than the diameter of the shaft.

In certain embodiments, the blades 318 and 320 of the cutting tool 304 of FIGS. 7 and 8 can be configured to create the shape of the screw tip illustrated in FIGS. 9-11, or any of the other self-tapping end portions described herein, without (or substantially without) burrs or material protrusions or extrusions that extend beyond the diameter of the shaft 336. Such burrs or protrusions extending beyond the diameter of the shaft can remove additional bone material from the pre-drilled hole in the bone (thereby widening its diameter) as the bone screw is driven into the bone, reducing the load-bearing capability of the bone screw and its pullout strength. Thus, the self-tapping bone screws illustrated in FIGS. 9-11 can exhibit load-bearing performance similar to existing self-tapping bone screws because the full thread height of the bone screws, or nearly the full thread height of the bone screws, can engage the bone when the bone screw is driven into the bone.

Figure 14:
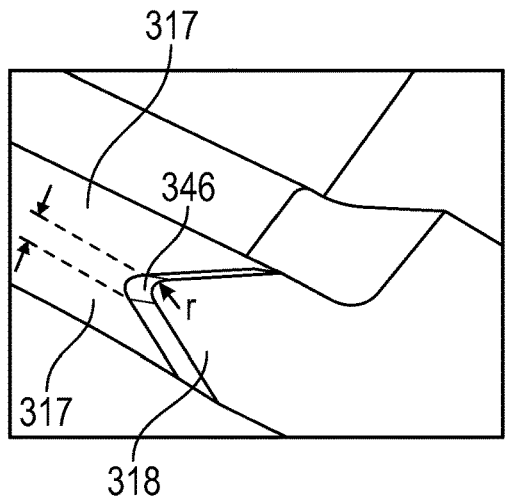
FIG. 14 illustrates a representative embodiment of one cutting blade of the cutting blades of the system of FIG. 7.
Figure 15:
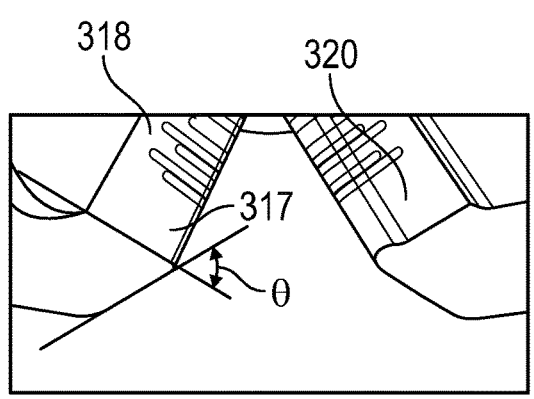
FIG. 15 illustrates another view of the representative embodiment of both cutting blades of the system of FIG. 7.

FIGS. 14 and 15 illustrate the cutting blades 318 and 320 of the apparatus 300, according to one embodiment. Referring to the blade 318 for purposes of illustration, the blade 318 can comprise a tapered or wedge-shape profile tapering to an edge 346. In certain embodiments the edge 346 can be curved, or can comprise a radius r. For example, in certain embodiments the edge 346 can comprise a radius r of 0.002 inch to 0.01 inch, such as 0.003 to 0.008 inch, or 0.005 inch. Additionally, the side surfaces 317 of the blade 318 can be tapered toward the edge 346, as shown in FIG. 14. The side surfaces 317 can define an angle θ (FIG. 15). In certain embodiments, the angle θ can be from 10° to 60°, such as 20° to 45°. In particular embodiments, the angle θ can be 30°.

Figure 16:
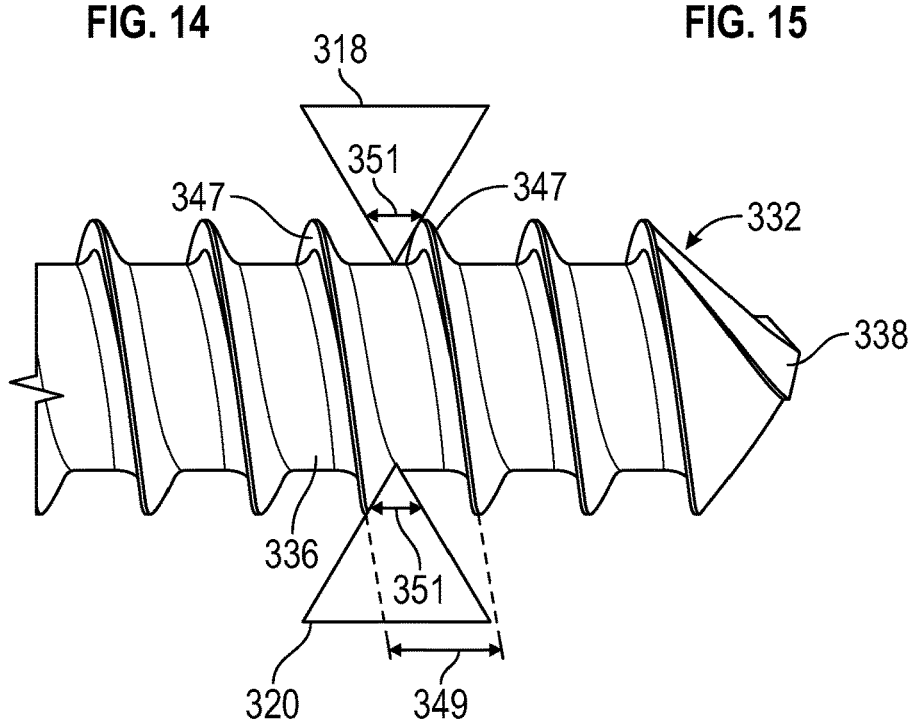
FIG. 16 schematically illustrates the cutting blades of the system of FIG. 7 positioned around a screw blank in preparation for cutting the screw blank, according to one embodiment.
Figures 17A, 17B:
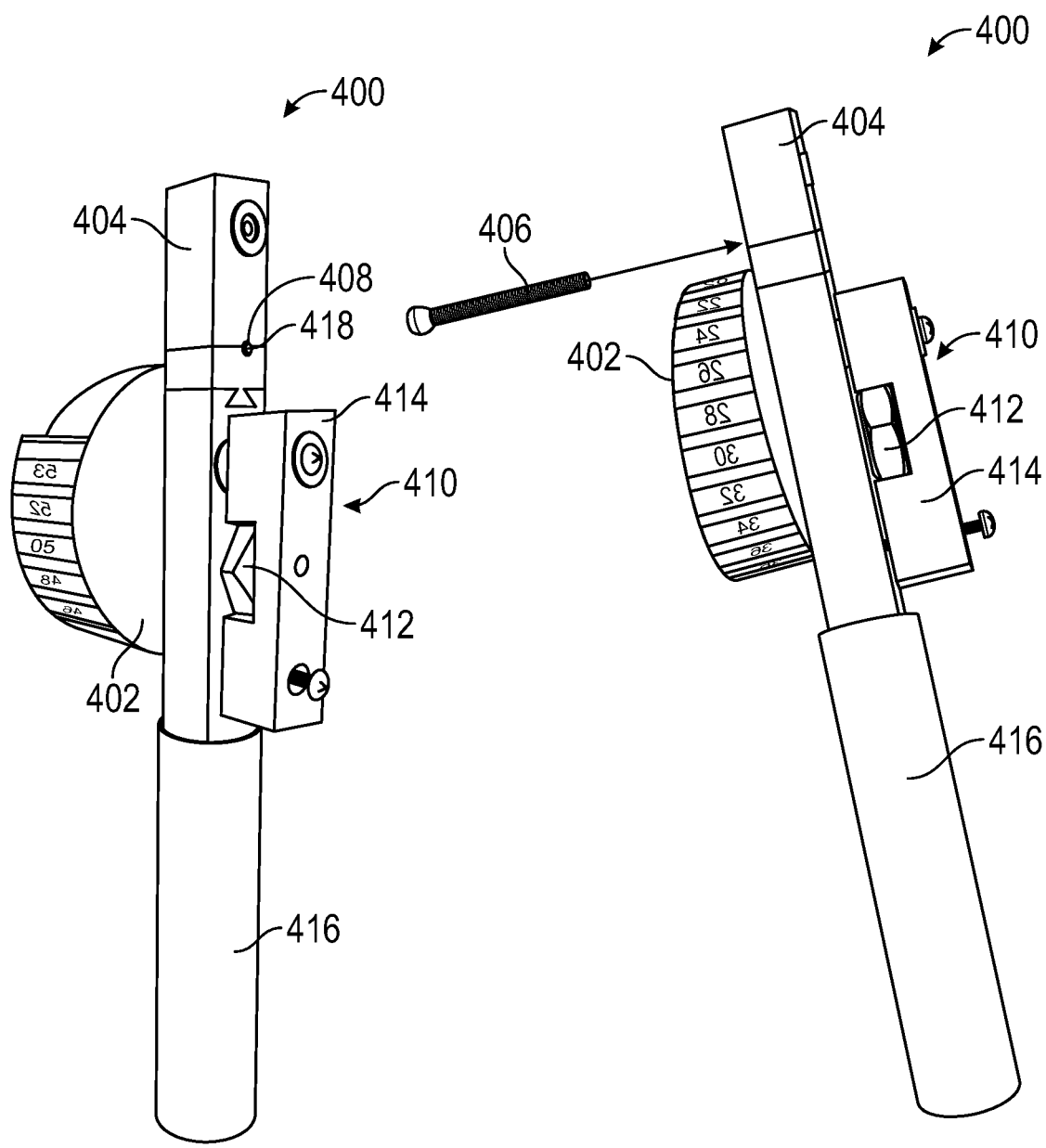
FIG. 17A is a first perspective view of another embodiment of a system for positioning and cutting a bone screw blank to a specified length and forming a self-tapping end portion on the screw blank.
FIG. 17B is a second perspective view of the system of FIG. 17A.

The width of the blades 318 and 320 and the angle θ of the blade surfaces 317 can be configured such that the blades 318 and 320 can be inserted between adjacent threads of the bone screw blanks to cut the bone screw blanks without damaging the threads. This is shown in FIG. 16, in which the blades or jaws 318 and 320 are shown schematically positioned between successive threads 347 with the tapered edges of the blades 318 and 320 adjacent or contacting the side surfaces of the threads 347. In certain embodiments, the angle of the side surfaces of the blades 318 and 320 can be the same, or nearly the same, as the angle of the side surfaces of the threads 347 such that the blades 318 and 320 move alongside the threads 347 as the bone screw blanks are cut without damaging or deforming the threads. The angle θ can be selected such that the width 351 of the portion of the blades 318 positioned between the threads 347 as the jaws close is less than or equal to the thread pitch 349 (FIG. 16). This can allow the edges of the blades to contact the shaft of the bone screw blank, and to be advanced toward each other without damaging the threads on either side.

In certain embodiments, the cutting action of the blades 318 and 320 can extrude/deform/displace or cause the material of the shaft 336 to plastically flow in a direction away from the bone screw head to create the wedge-shaped, self-tapping end portion 334 illustrated in FIGS. 9-11. Such plastic flowing action can be facilitated by the radiused edges of the blades 318 and 320, as described above, resulting in a substantially burr-free, self-tapping end portion, and without increasing the diameter of the shaft at the location of the cut.

In certain embodiments, the self-tapping end portions of the bone screw blanks can include a notch or slot shaved/ground/formed in the tip, which can be performed in a separate step after cutting of the bone screw blank.

The following is an example of using the system described above in a TPLO procedure. A canine patient's tibia bone can be prepared by performing an osteotomy at the proximal end and rotating the tibial plateau (FIG. 3). Pilot holes can be drilled in the tibia and in the excised portion of the proximal tibia at the location were bone screws are to be placed for the TPLO bone plate. A first length can be determined by measuring the depth of the holes with a depth gauge. Based on the measured first length, a second length can be determined which will allow a bone screw to be inserted through the bone plate, through the hole in the bone, and to protrude a distance of 1 mm to 3 mm out of the opposite side of the bone. A bone screw blank can be cut to the second length and, where specified, a self-tapping end portion can be formed on the cut bone screw blank using any of the systems described herein. The resulting bone screw can then be advanced through the bone plate and into the bone. This process can be repeated to form bone screws for each of the holes of the bone plate. A similar process can be employed for other types of orthopedic procedures (human or veterinary), including any of the other procedures described herein.

Second Representative Embodiment

Figure 18A:
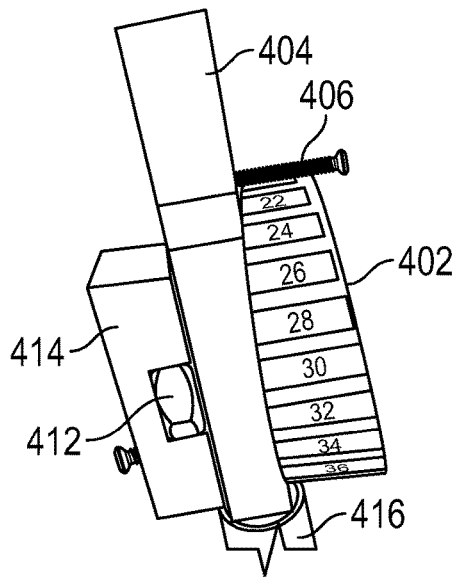
FIGS. 18A-18F illustrate a method for cutting a bone screw blank to a specified length and forming a self-tapping end portion on the screw blank using the system of FIG. 17A.
Figure 18B:
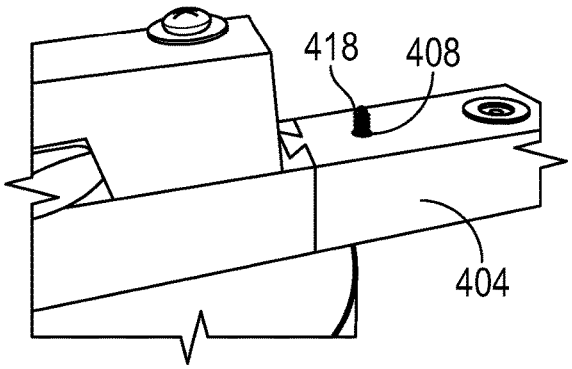
Figure 18C:
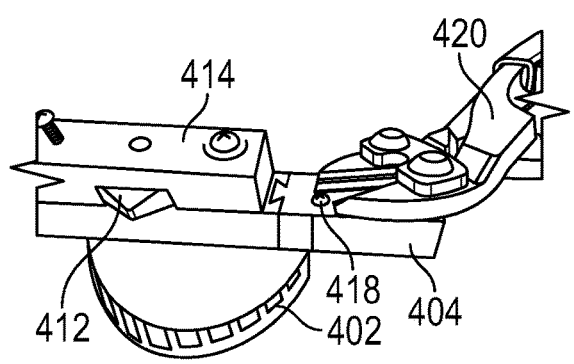
Figure 18D:
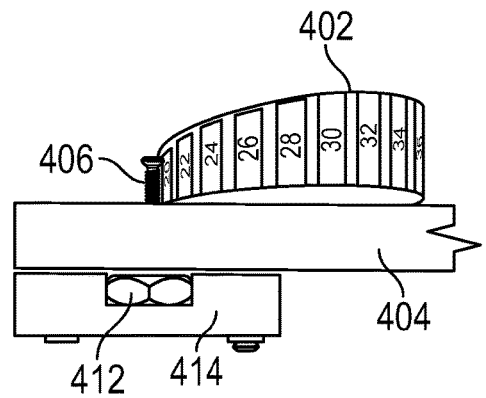
Figure 18E:
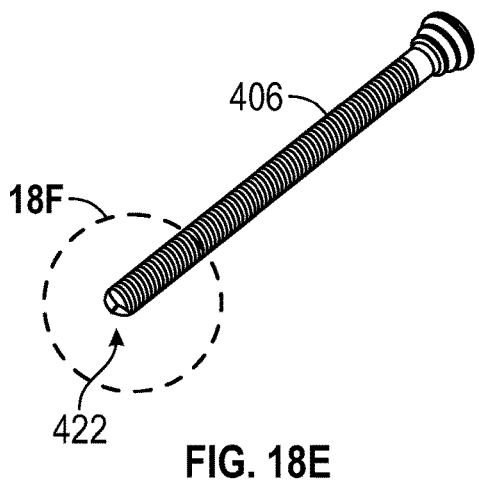
Figure 18F:
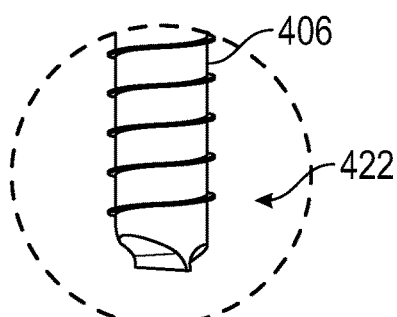

FIGS. 17A-18F illustrate another embodiment of a system, apparatus, or tool 400 (FIGS. 17A and 17B) and a method for using the tool 400 for positioning and cutting bone screw blanks to a specified size and forming a self-tapping end portion on the bone screws (FIGS. 18A-18F). A rotatable member configured as a wheel or drum 402 can be coupled to a frame member 404 which is coupled to a handle 416. The drum 402 can comprise a plurality of openings or bores around its circumference. A thickness of the drum 402 can vary about its circumference such that the openings have varying, specified lengths corresponding to selected screw lengths. A bone screw blank 406 inserted into an opening in the drum 402 (FIG. 18A) can protrude through an opening 408 defined in the frame member 404 (FIG. 18B) for cutting to the length corresponding to the opening. The protruding tip 418 of the screw 406 can be cut with a hand (e.g., shearing) tool 420 (FIG. 18C). A tapping assembly 410 comprising a die 412 mounted in a frame 414 can then be rotated into position and axially aligned with the cut bone screw (FIG. 18D) for forming a self-tapping end portion 422 on the bone screw (FIGS. 18E and 18F).

Third Representative Embodiment

Figure 19A:
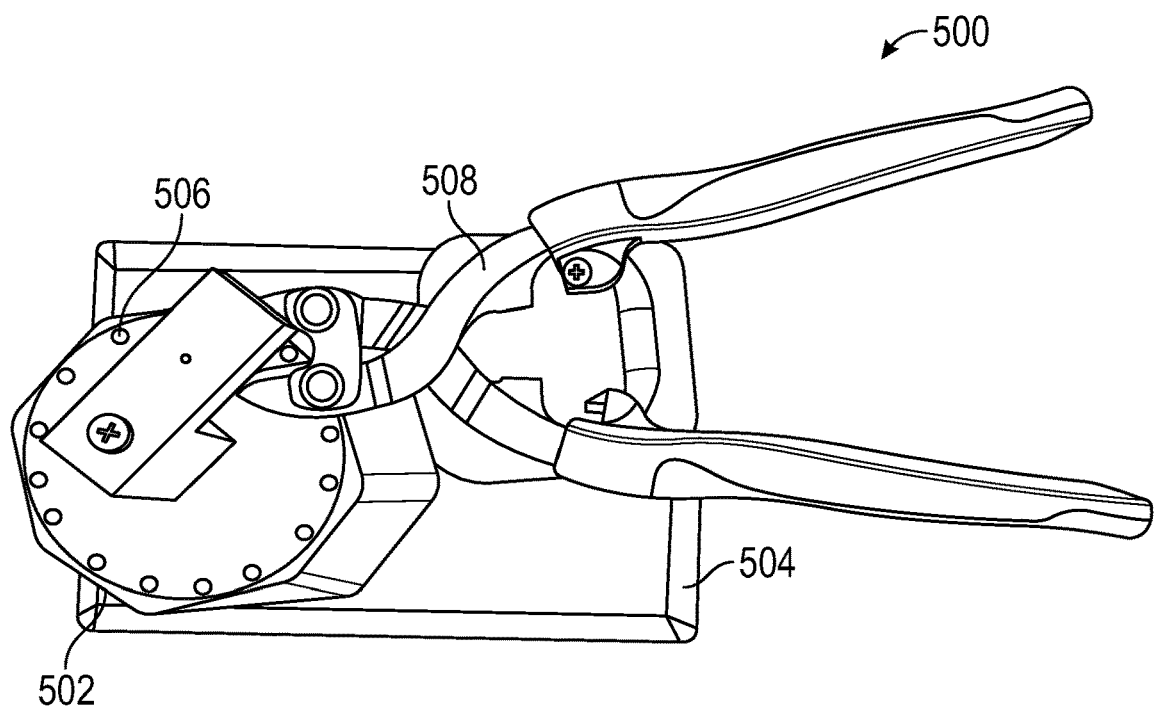
FIG. 19A is a top view of another embodiment of a system for positioning and cutting a bone screw blank to a specified length and forming a self-tapping end portion on the screw blank.
Figure 19B:
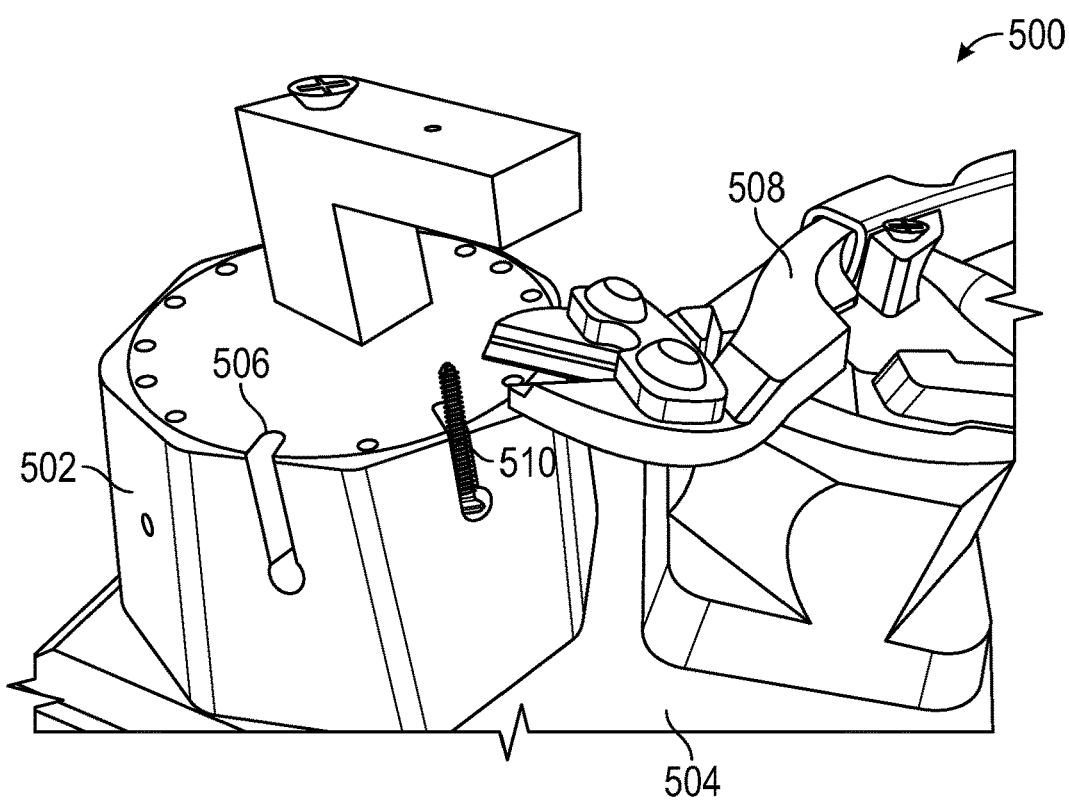
FIG. 19B is a magnified, perspective view of a portion of the system of FIG. 19A.

FIGS. 19A and 19B illustrate another embodiment of a system, apparatus, or tool 500 for positioning and cutting bone screw blanks to a specified length and forming a self-tapping end portion on the bone screws. The system 500 can comprise a rotatable member, wheel, or drum 502 coupled to a base 504. The rotatable member 502 can comprise a plurality of openings or bores 506 around its circumference. The openings 506 can have varying depths corresponding to specified screw lengths. A cutting assembly (e.g., diagonal cutters, shears, or snips) 508 can be mounted to the base 504 adjacent the rotatable member 502. The rotatable member 502 can be rotated relative to the cutting assembly 508 to position a bone screw blank 510 to be cut by the cutting assembly. The cutting assembly 508 can cut the bone screw blank 510 to the length specified by the opening 506 of the rotatable member 502 in which the bone screw blank 510 is received. The cutting assembly 508 can also form a self-tapping end portion on the bone screw blank 510 using any of the methods and tools described herein.

Fourth Representative Embodiment

Figure 20:
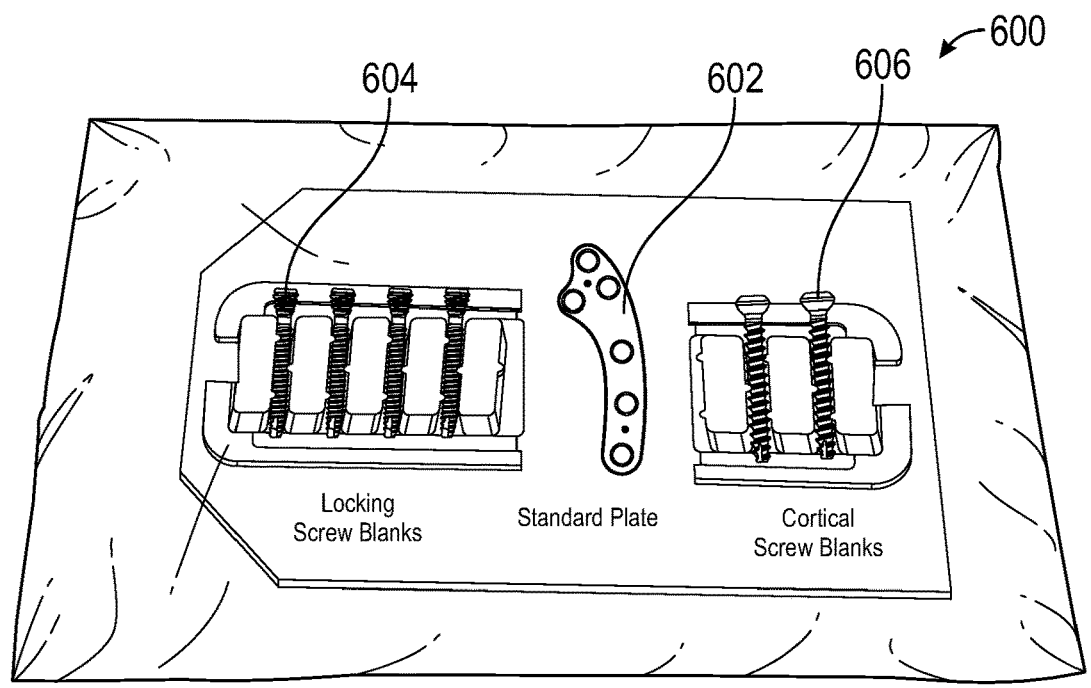
FIG. 20 illustrates an embodiment of a kit or surgical pack including a bone plate and a plurality of bone screw blanks.
Figure 21:
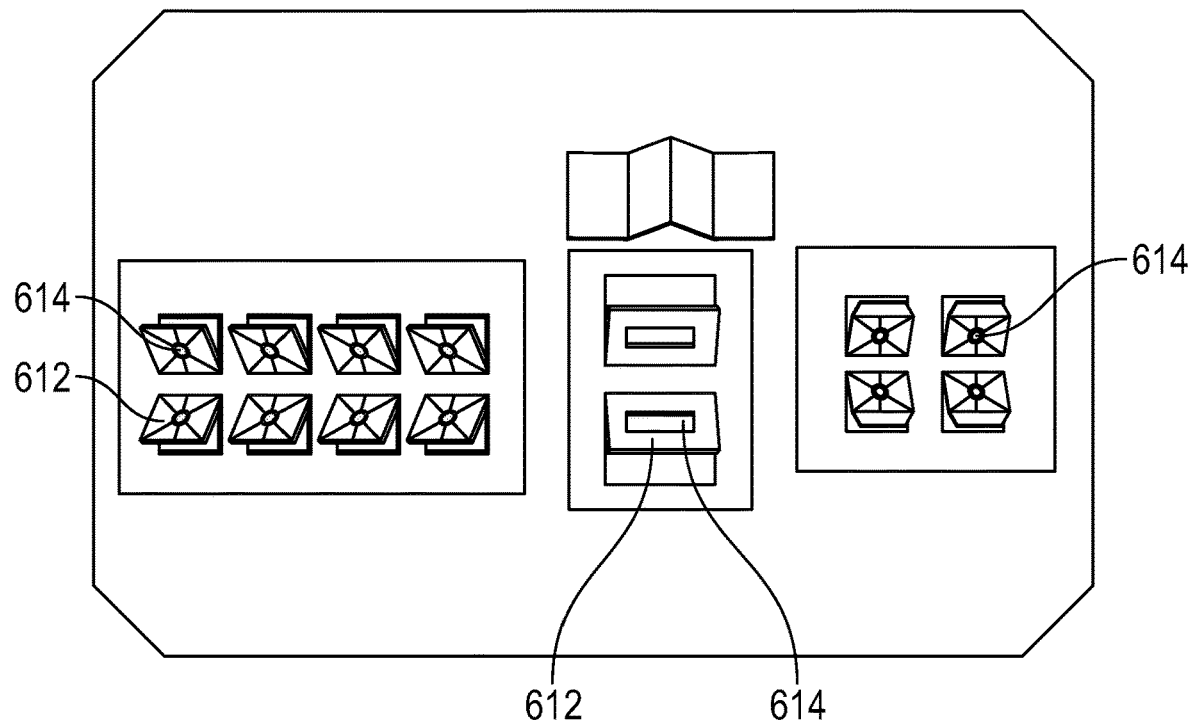
FIG. 21 illustrates an embodiment of a base for a kit or surgical pack including a bone plate and a plurality of bone screw blanks.

FIGS. 20 and 21 illustrate an orthopedic implant kit 600, according to one embodiment. In the illustrated embodiment, the kit can include an orthopedic implant (e.g., a bone plate or other fixation member) 602 and a plurality of bone screw blanks 604 and 606 of specified size, type, thread pitch, etc., corresponding to the implant 602. For example, in the illustrated embodiment the kit comprises a TPLO bone plate 602, four locking bone screw blanks 604, and two cortical bone screw blanks 606, although other configurations are possible.

In certain embodiments, the bone screw blanks, implant, etc., can be secured/engaged/retained on a base 610, such as a cardboard, paperboard, or cardstock base 610 (FIG. 21). The base 610 can comprise a plurality of tabs 612 arranged in pairs and configured to be bent upwardly relative to the surface of the base 610 (FIG. 21). The tabs 612 can comprise openings 614 configured to receive a bone screw, an implant, etc. Inserting the bone screw blanks or implant through the openings of a respective pair of tabs can suspend the blank or implant above the surface of the base 610, as shown in FIG. 21. In certain embodiments, the bone screw blanks, implant(s), and/or the base member can be sterilized and packaged in one or more packages (e.g., polymer pouches, such as a high-density polyethylene (HDPE) pouches or packages). For example, the bone screw blanks and the implant can be sterilized by gamma irradiation and/or ethylene oxide before or after packaging. This can allow the kits to be transported and/or stored in a non-sterile environment while maintaining the contents in a surgical aseptic or sterile condition until implantation. As used herein, the term "surgically aseptic" refers to the absence of microorganisms, such as achievable by autoclaving.

Figure 22A:
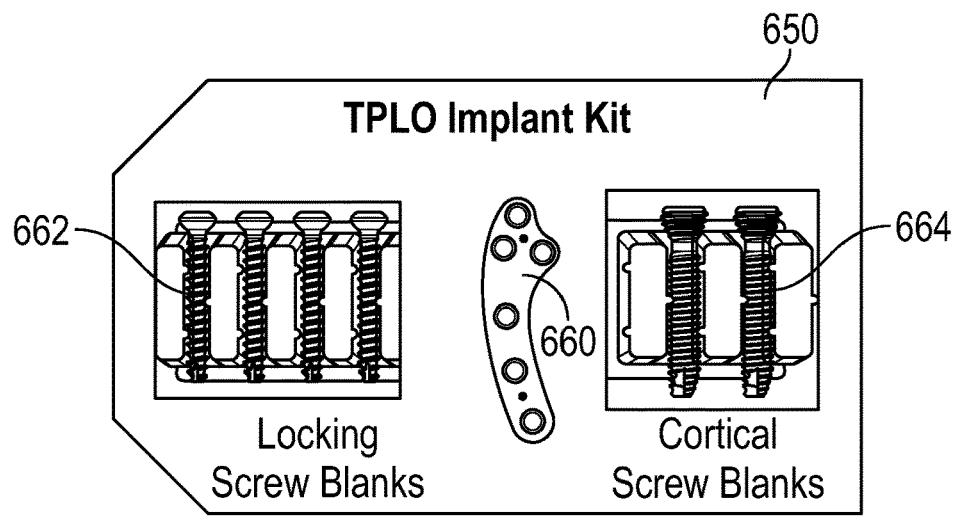
FIGS. 22A-22E illustrate embodiments of various kits or surgical packs for different procedures, the kits including a bone plate and a plurality of bone screw blanks.
Figure 22B:
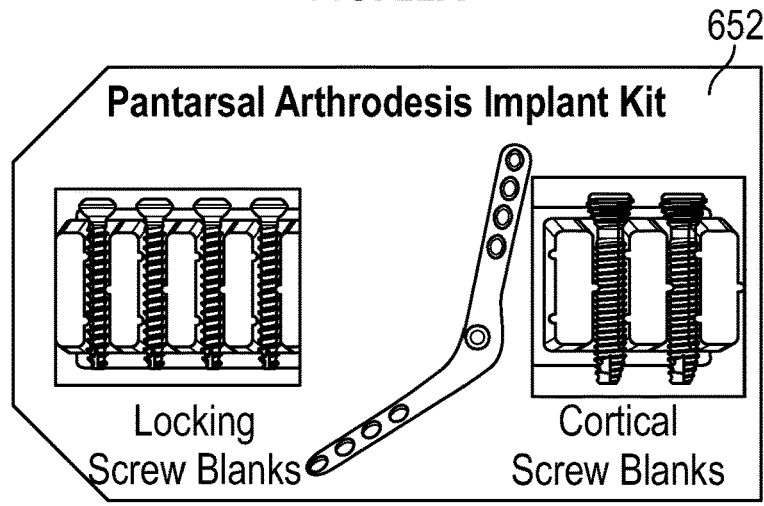
Figure 22C:
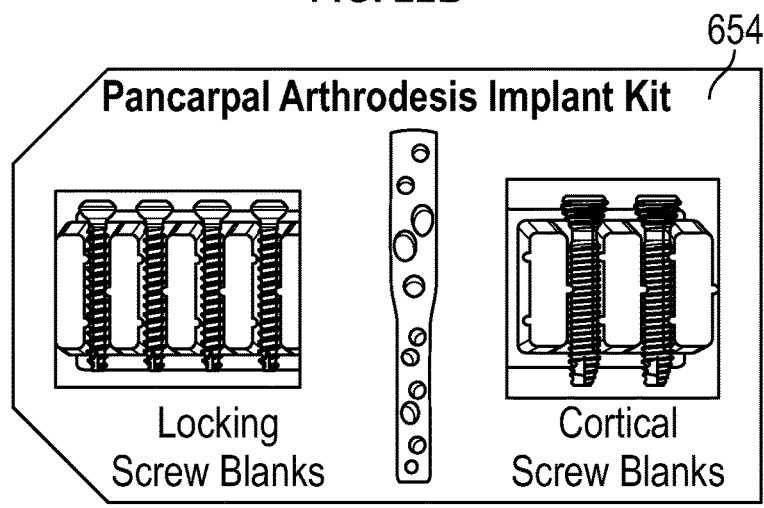
Figure 22D:
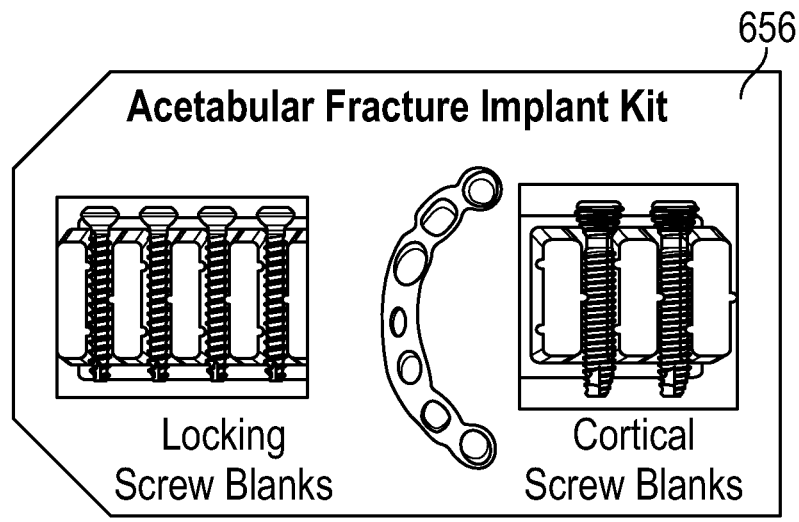
Figure 22E:
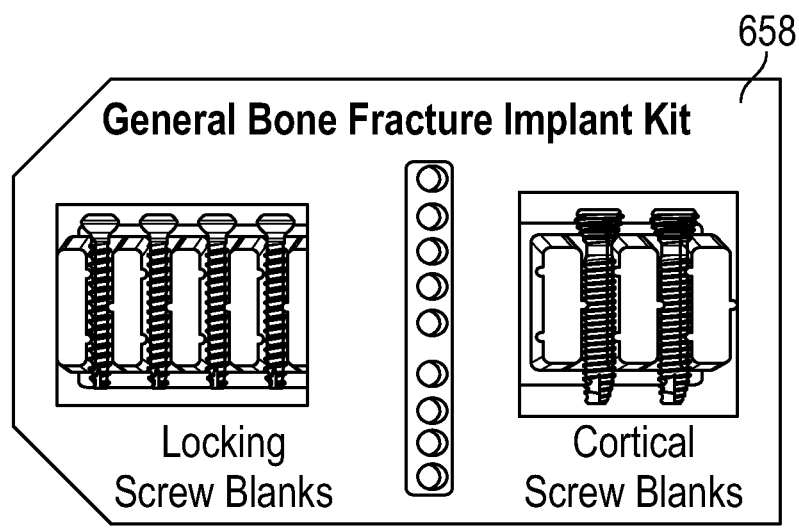

FIGS. 22A-22E illustrate a variety of embodiments of kits including implants for various veterinary orthopedic procedures, including a TPLO implant kit 650 (FIG. 22A), a pantarsal arthrodesis implant kit 652 (FIG. 22B), a pancarpal arthrodesis implant kit 654 (FIG. 22C), an acetabular fracture implant kit 656 (FIG. 22D), and a general bone fracture implant kit 658 (FIG. 22E). Each kit shown in FIGS. 22A-22E can include an implant 660, a plurality of locking bone screw blanks 662, and a plurality of cortical bone screw blanks 664 (FIG. 22A).

In certain embodiments, the bone screw blanks 604 and 606 shown in FIG. 20 and the bone screw blanks 662 and 664 shown in FIGS. 22A-22E can be the same as or similar to the bone screw blank 100 shown in shown in FIGS. 5A-5D or the bone screw blank 200 shown in FIGS. 6A-6G.

Fifth Representative Embodiment

FIGS. 23A-23E illustrate another embodiment of a system, apparatus, or tool 700 for positioning and cutting bone screw blanks to a specified length and forming a self-tapping end portion on the bone screws. FIGS. 23E-25B illustrate a method for using the system 700.

The system 700 can comprise a mounting assembly 702 comprising two clamp members 704. Mating surfaces of the clamp members 704 can define openings 706 configured to receive a locking bone screw and/or a cortical bone screw. A position adjustment member 708 can be movable along a support member 710 relative to the clamp members 704. The support member 710 can comprise a length scale (FIG. 23C). The system 700 can further comprise a rotatable knob 712 configured to move the clamp member 704 toward and away from one another.

Figure 24:
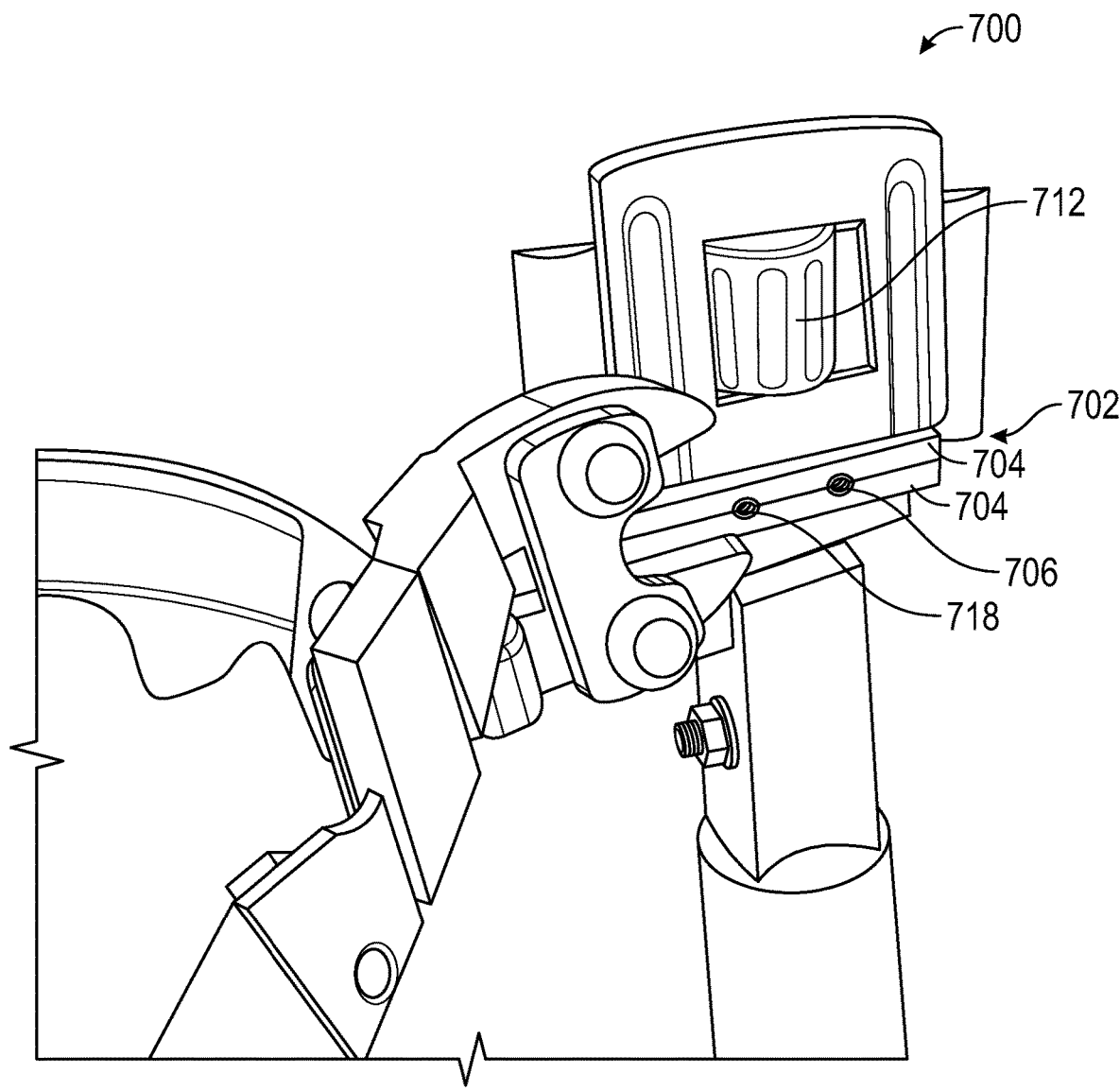
FIGS. 24-25B illustrate a method for using the system of FIGS. 23A-23E to cut a bone screw blank to a specified length and form a self-tapping end portion on the screw blank.
Figure 25A:
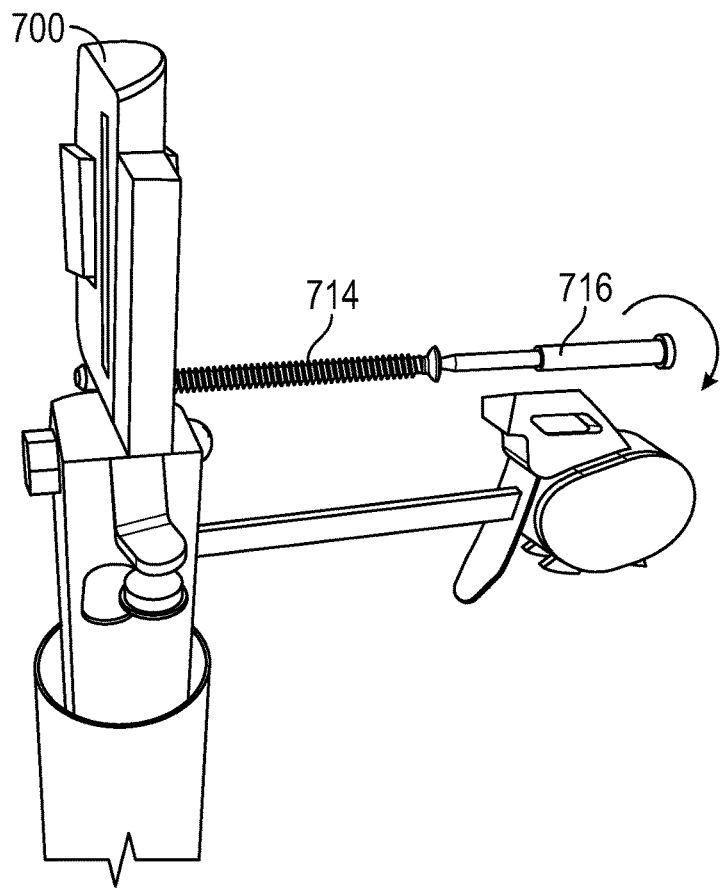
Figure 25B:
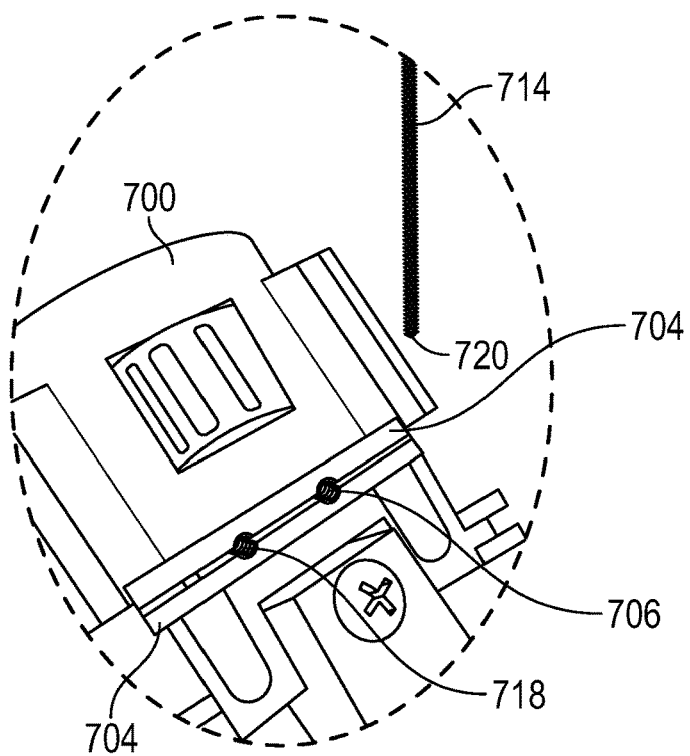

A bone screw blank 714 can be received in the specified opening 706 between the clamp members 704 (FIG. 23E). A desired length of the bone screw blank 714 can be set using the position adjustment member 708 on one side of the clamp members 704 (FIG. 23E). An end of the bone screw blank 714 extending from the opposite side of the clamp members 704 can be cut (e.g., with a cutting assembly similar to the cutting assemblies described elsewhere herein) (FIG. 24). In certain embodiments, plates at the mating surfaces of the clamp members 704 can comprise die cutting features 718 (FIGS. 24 and 25B). After the bone screw blank 714 has been cut to the specified length, the cut bone screw can be withdrawn from the opening 706 defined by the clamp members 704 (e.g., by rotating the cut bone screw with a screw driver 716) (FIG. 25A) and the die cutting features 718 of the clamp members 704 can form a self-tapping end portion 720 on the bone screw as it is withdrawn (FIG. 25B).

Figure 26A:
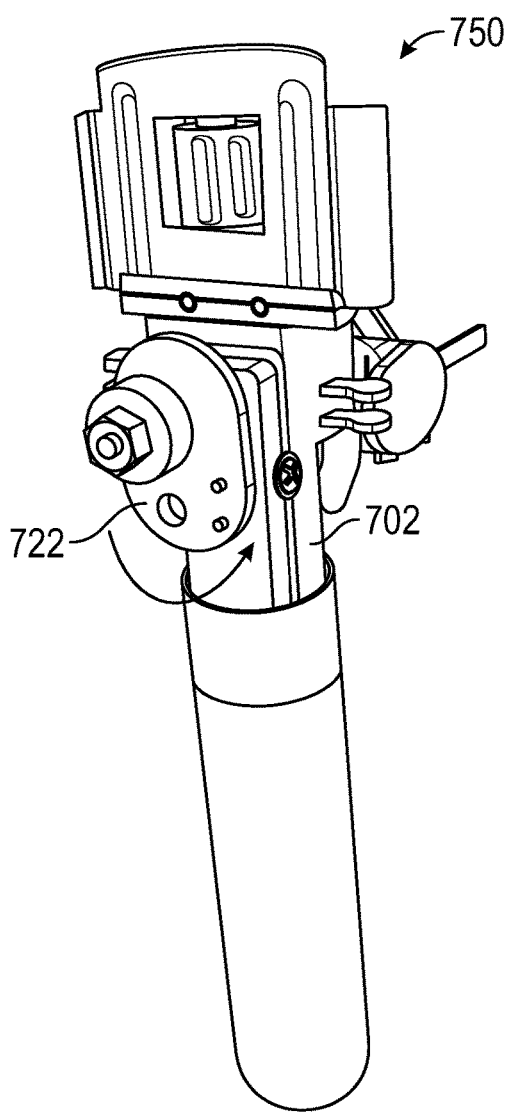
FIGS. 26A-26C illustrate another embodiment of a system for positioning and cutting a bone screw blank to a specified length and forming a self-tapping end portion on the screw blank, similar to the system of FIGS. 23A-23E but including a die member 722 to form the self-tapping end portion on the screw blank.
Figure 26B:
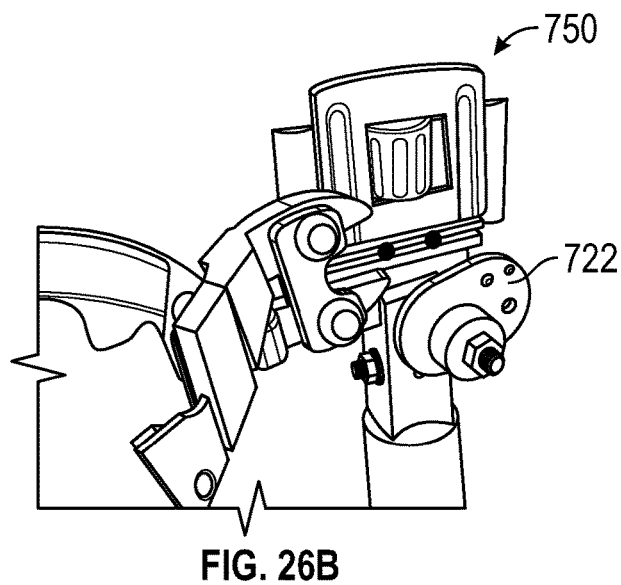
Figure 26C:
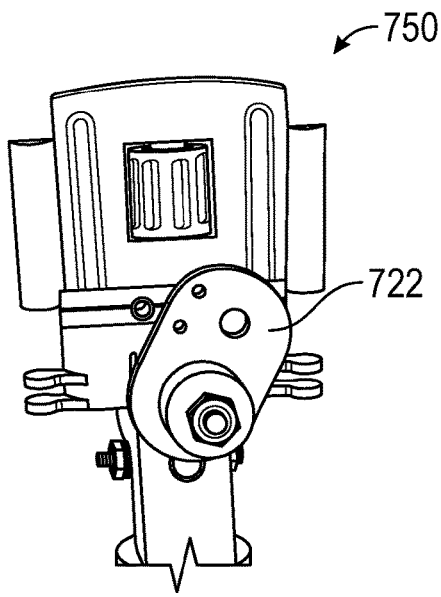
Figure 26D:
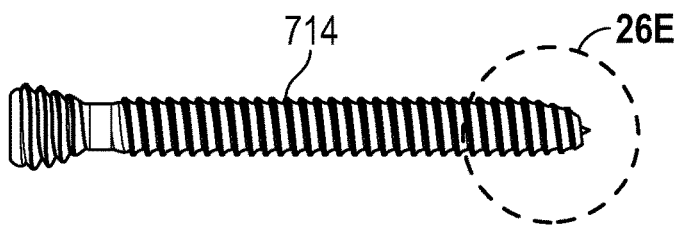
FIGS. 26E and 26D illustrate a bone screw with a self-tapping end portion formed using the system of FIGS. 26A-26C.
Figure 26E:
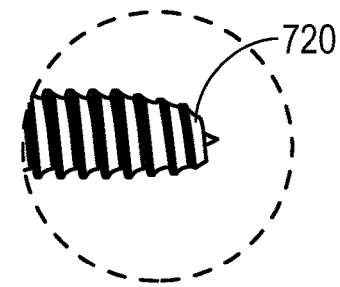

In another embodiment shown in FIGS. 26A-26E, a system 750, similar to the system 700, can further comprise a tip shaver/die member 722, which can be rotatably coupled to the mounting assembly 702. Once the bone screw blank 714 is cut to the specified length (FIG. 26B), the die member 722 can be rotated into place (FIG. 26C), and the cut bone screw can be advanced into the die member 722, which can form a self-tapping end portion 720 on the bone screw (FIGS. 26D and 26E).

Sixth Representative Embodiment

Figure 27:
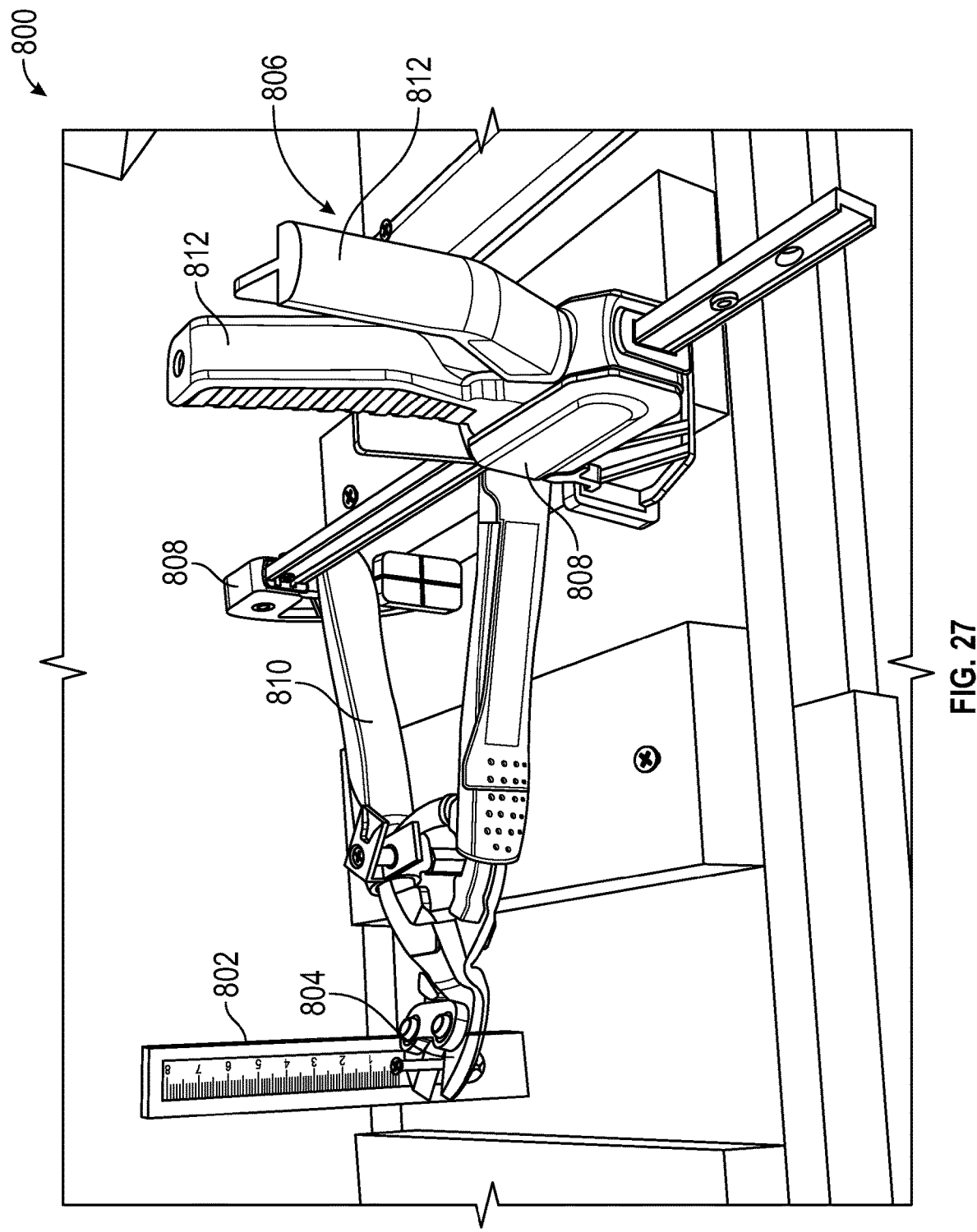
FIG. 27 illustrates another embodiment of a system for positioning and cutting a bone screw blank to a specified length and forming a self-tapping end portion on the screw blank.
Figure 28:
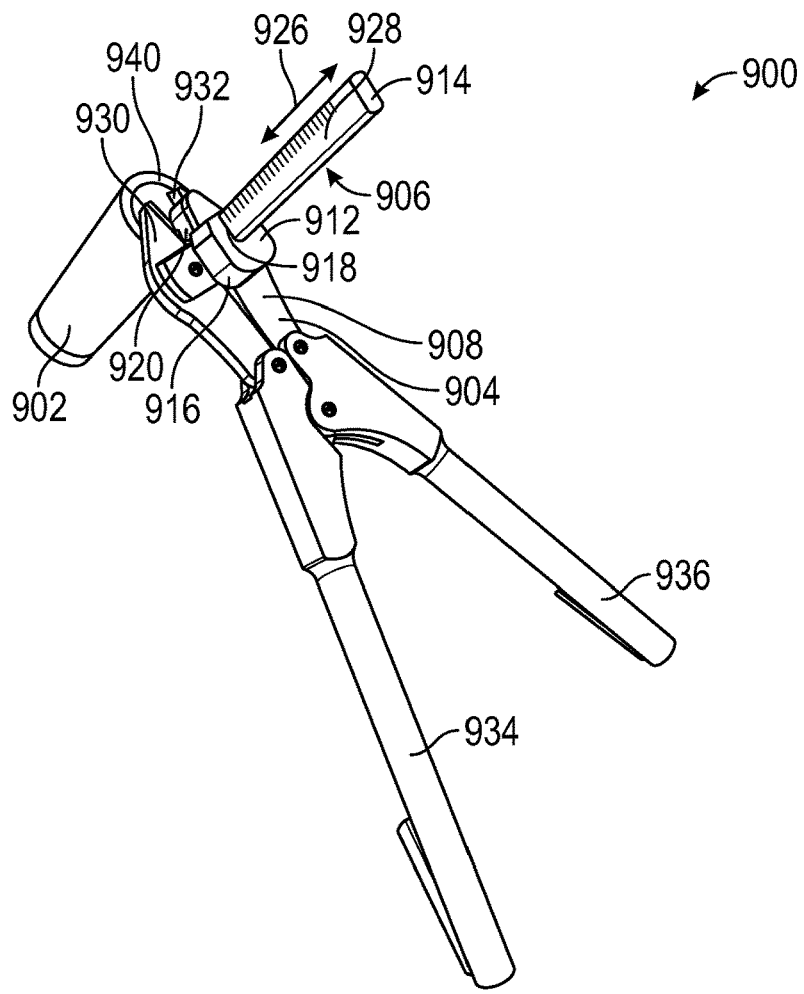
FIG. 28 is a first perspective view of another embodiments of a system for positioning and cutting a bone screw blank to a specified length and forming a self-tapping end portion on the resulting cut screw.
Figure 29:
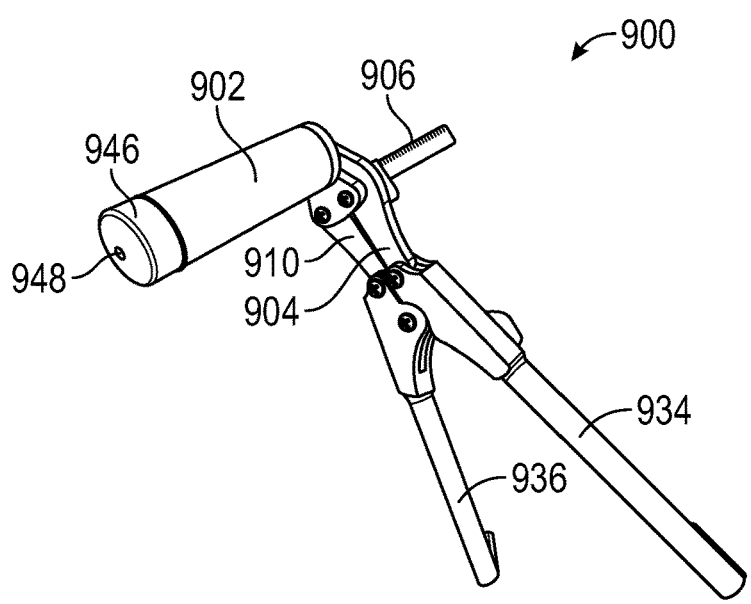
FIG. 29 is a second perspective view of the system of FIG. 28.

FIG. 27 illustrates another embodiment of a system, apparatus, or tool 800 for positioning and cutting bone screw blanks to a specified length and forming a self-tapping end portion on the bone screws. The system 800 shown in FIG. 27 can be mounted on a table or other surface. The bone screw blank can be mounted in a positioning assembly 802 and cutting members 804 of a cutting apparatus or assembly configured to cut the bone screw blank to a desired length can be actuated using a clamping apparatus 806. The clamping apparatus 806 can include jaws or clamping members 808 positioned on either side of lever members 810 of the cutting apparatus and clamps or handle members 812 configured to be moved toward one another to actuate the lever member 810 and the cutting members 804 to cut the screw blank.

Seventh Representative Embodiment

FIGS. 28-34B and 39-43B illustrate another embodiment of a system, tool, or apparatus 900 for positioning and cutting bone screw blanks to a specified length and forming a self-tapping end portion on the bone screws. The apparatus 900 can comprise a cutting assembly (e.g., cutting tool) 904 and a position adjustment assembly 906 (e.g., similar to the apparatus 300 shown in FIGS. 7 and 8, as described above). In some embodiments, as shown in FIGS. 28-34A and 39-41, the cutting assembly 904 and the position adjustment assembly 906 can be coupled together (e.g., directly coupled to one another or indirectly coupled to one another through an intervening component). For example, the position adjustment assembly 906 can be disposed on and coupled to a first side 908 of the cutting assembly 904 (FIGS. 28, 30-33, and 39).

In some embodiments, the apparatus 900 can further comprise a container (container portion or receptacle) 902 disposed on and coupled to a second side 910 of the cutting assembly 904 (FIGS. 29, 32, 34A, 40, and 41).

The position adjustment assembly 906 is configured to receive a bone screw blank (such as one of the bone screw blanks described herein) and position the bone screw blank relative to the cutting assembly 904. For example, the position adjustment assembly 906 can include a housing or mounting member 912 and a measurement member 914, the mounting member 912 configured to slide along a length of the measurement member 914 and relative to the cutting assembly 904 (FIGS. 28 and 30-33).

In some embodiments, the measurement member 914 can be coupled to the first side 908 of the cutting assembly 904 and the mounting member 912 can slide along the measurement member 914, relative to the cutting assembly 904 (e.g., toward and away from the first side 908). In some embodiments, a shown in FIGS. 30-33 and 39, the measurement member 914 can be coupled to the first side 908 of the cutting assembly 904 by a mounting bracket 970. For example, an end of the measurement member 914 can be directly coupled to the mounting bracket 970 and the mounting bracket 970 can be directly coupled to the first side 908 of the cutting assembly 904.

Figure 30:
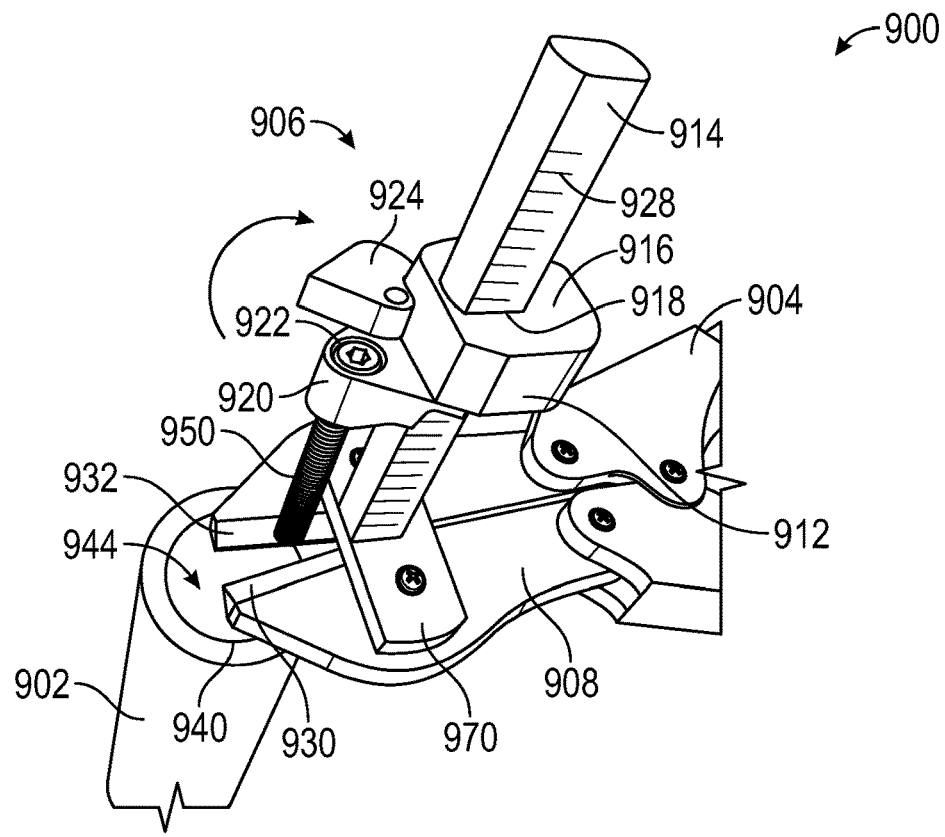
FIG. 30 is a magnified view of a portion of the system of FIG. 28, illustrating a cap of a position adjustment assembly of the system in an open position and a screw blank received within a portion of the position adjustment assembly.
Figure 31:
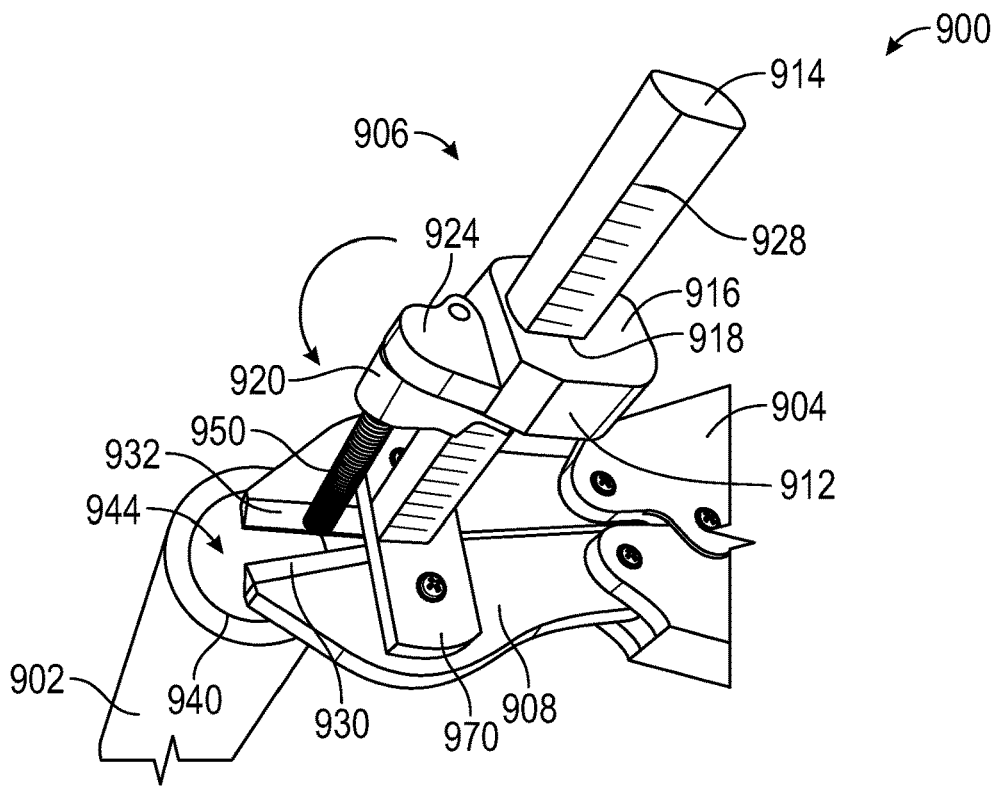
FIG. 31 is a magnified view of a portion of the system of FIG. 29, illustrating the cap of the position adjustment assembly in a closed position.
Figure 32:
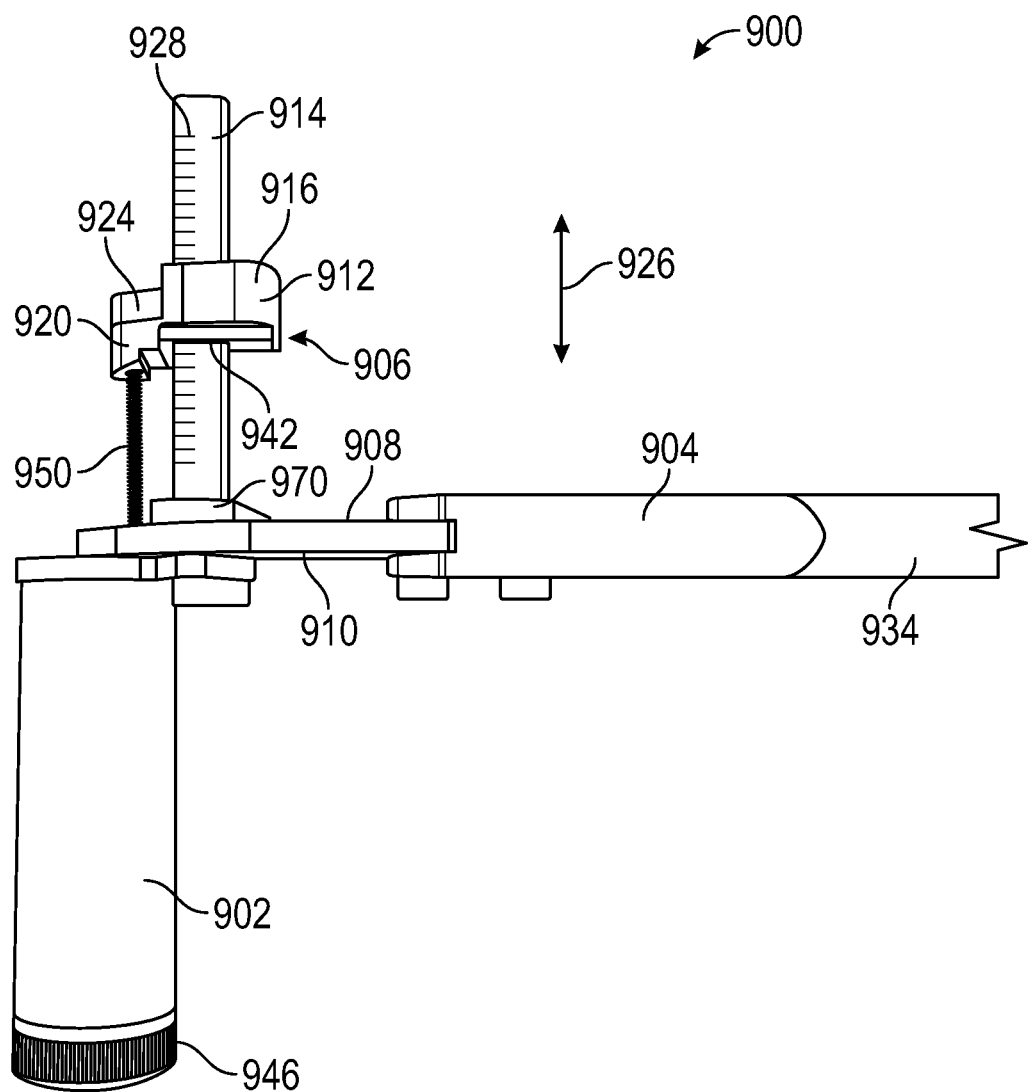
FIG. 32 is a side view of the system of FIG. 28.
Figure 33:
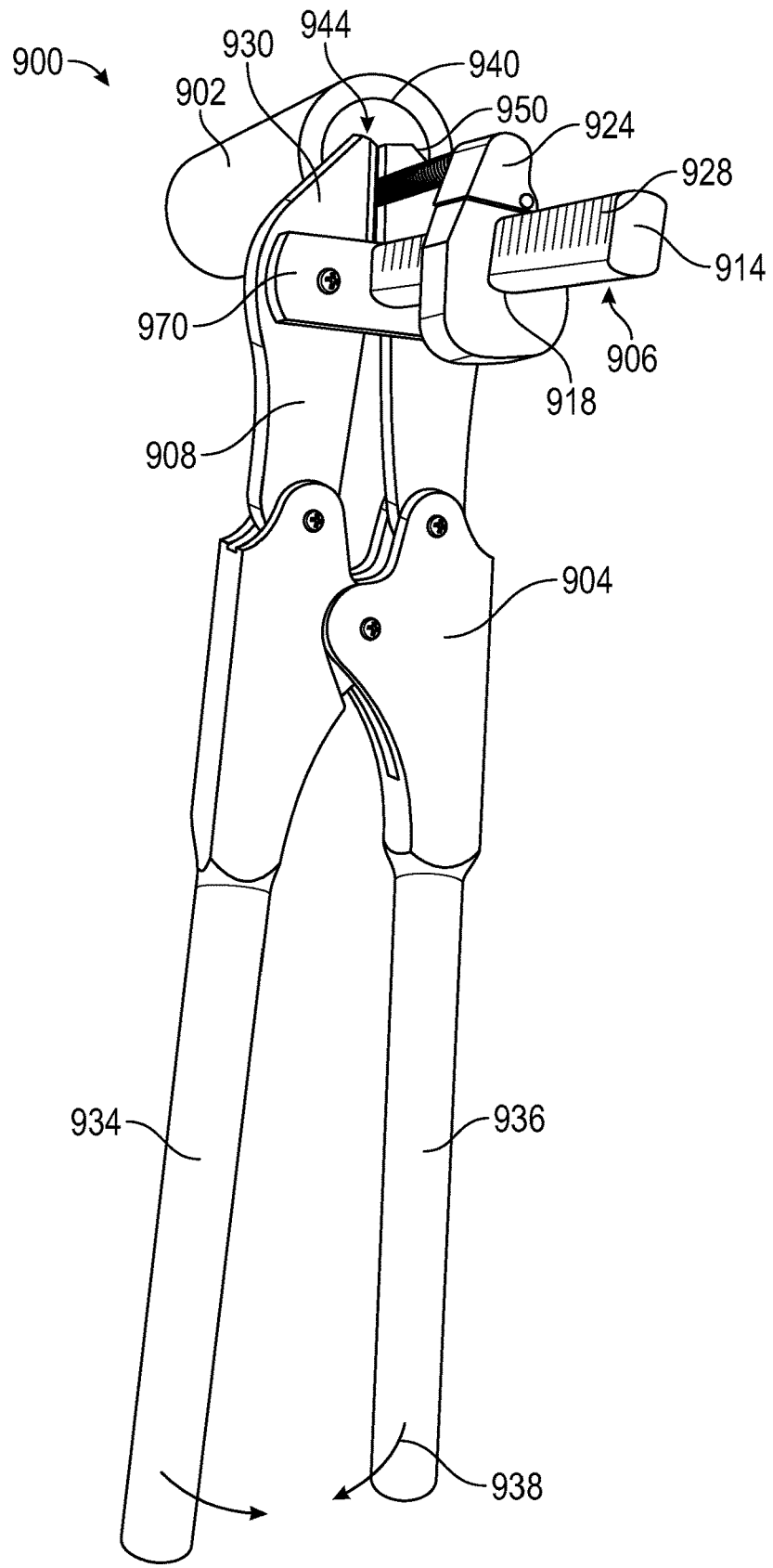
FIG. 33 another perspective view of the system of FIG. 28, illustrating actuating of blades of a cutting assembly of the system into a closed position for cutting the screw blank to the specified length.
Figure 35:
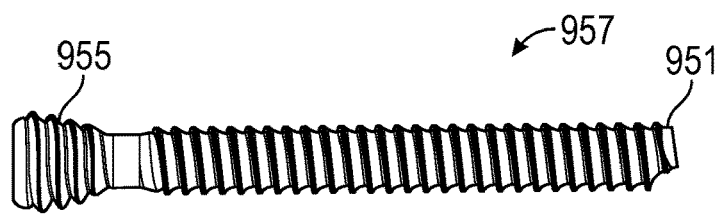
FIG. 35 is a side view of an exemplary cut screw created from a screw blank cut by the system of FIG. 28.

As shown in FIGS. 28 and 30-33, the mounting member 912 can include a first (e.g., carriage) portion 916 defining an opening (or aperture) 918 configured to receive the measurement member 914. As such, the mounting member 912 can slide along the measurement member 914 via the opening 918. The mounting member 912 can further include a second (e.g., mounting) portion 920 coupled to the first portion 916 and including an opening 922 configured to receive a second end portion (including a head) of a bone screw blank 950 (FIG. 30). The second portion 920 and a shape of the opening 922 can be configured such that the second end portion of the bone screw blank 950, including a head of the bone screw blank 950, is held in the second portion 920. In certain embodiments, the second portion 920 can be threaded to receive the bone screw blank 950, such as threaded to engage the threads of the shank and/or the threads of a locking head of the bone screw blank 950. Further, the mounting member 912 can include a third portion, configured as a pivotable cap 924, configured to pivot (or rotate) relative to the second portion 920 (FIGS. 30-33). Thus, after loading the bone screw blank 950 into the second portion 920 (as shown in FIG. 30), the cap 924 can be pivoted over the second portion 920 to cover the opening 922 and hold the bone screw blank 950 firmly in place within the mounting member 912 (FIG. 31). For example, when the cap 924 is in the closed position (as shown in FIGS. 31-33) the bone screw blank 950 can be prevented from translating, at least along an axis 926 (FIGS. 28 and 32), relative to the mounting member 912.

The measurement member 914 can include a scale or measurement markings 928 arranged along its length (e.g., in a direction of the axis 926). As described further below, the measurement markings 928 can correspond to a plurality of specified lengths for the bone screw blank (e.g., after cutting). The first portion 916 of the mounting member 912 can comprise an inner edge 942 (FIG. 32) that is configured to be aligned with a selected measurement marking 928 that corresponds to a specified length for the cut bone screw blank 950.

The cutting assembly 904 can comprise a plurality of blades configured to be actuated by handles of the cutting assembly 904. For example, as shown in FIGS. 28-31, 33, and 39, the cutting assembly 904 can comprise a pair of opposed jaws/cutting edges/blades 930 and 932 coupled to respective members configured as handles 934 and 936. Pivoting the handles 934 and 936 together (e.g., toward one another, as shown by arrow 938 in FIG. 33) can bring the blades 930 and 932 together in the manner of shears, scissors, snips, diagonal cutters, diagonal pliers, wire cutters, or bolt cutters.

In some embodiments, the blades 930 and 932 can be configured similarly to the blades 318 and 320, as described above with reference to FIGS. 7-8 and 14-16.

The container 902 can comprise an opening 940 oriented toward the mounting member 912 (FIGS. 28, 30, 31, and 33). For example, the opening 940 can be disposed at a first end of the container 902 which is coupled to the second side 910 of the cutting assembly 904. The opening 940 can be an opening into an interior cavity 944 of the container 902. In some embodiments, the container 902 can be configured as a tube or cylinder with a hollow interior. However, in alternate embodiments, the container 902 can have a different shape, such as having a square, oblong, or rectangular cross-section.

The interior cavity 944 of the container 902 can be configured to receive a cut end portion of the bone screw blank 950, after being cut with the cutting assembly 904. In some embodiments, a second end (which is arranged opposite the first end) of the container 902 can include a removable cap 946 (FIGS. 29, 32, 34A, 34B, and 41-42). For example, the cap 946 can be configured to screw onto the second end of the container.

Figure 36:
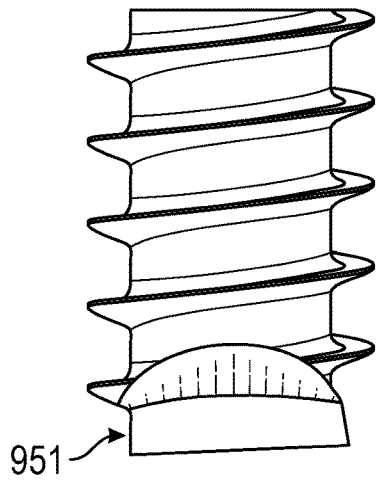
FIG. 36 is a magnified view of the exemplary cut screw of FIG. 35 after being cut by the system of FIG. 28.
Figure 37:
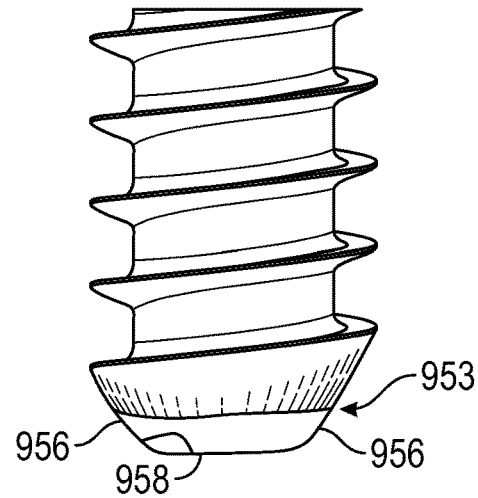
FIG. 37 is first, magnified side view of the exemplary cut screw of FIG. 35 after being honed by the deburring member of FIG. 34B.
Figure 38:
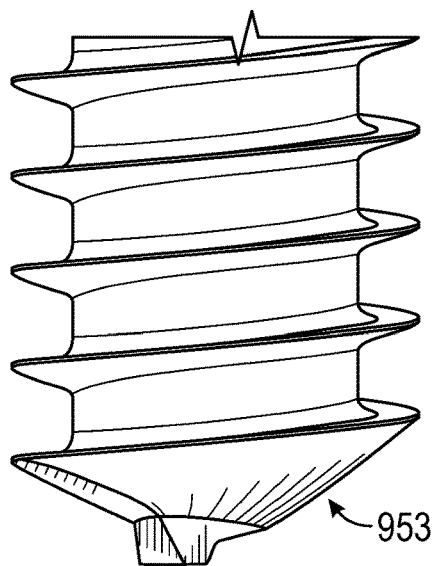
FIG. 38 is a second, magnified side view of the cut screw of FIG. 35 after being honed by the deburring member of FIG. 34B.

In some embodiments, as shown in FIGS. 29, 34A, 34B, and 42, the cap 946 can include an aperture or opening 948. A deburring member 952 can be coupled to or integrated with (e.g., molded as one piece) an interior of the cap 946 (FIG. 41). The deburring member 952 can include a plurality of blades 954 (FIGS. 42-43B). When the deburring member 952 is coupled with the cap 946, the blades 954 are disposed adjacent the opening 948. As such, the blades 954 can be configured to receive a cut, first end portion 941 of the cut bone screw 957 (as shown in FIG. 34A) and deburr and/or hone the first end portion 951 to create a honed, self-tapping end portion 953 on the cut bone screw 957 (as shown in FIGS. 37 and 38). In some embodiments, the first end portion 941 of the cut bone screw 957, after cutting and before honing, may be self-tapping (FIG. 36). However, the honed, self-tapping end portion 953, created after honing with the deburring member 952, may have a more refined self-tapping end portion with increased self-tapping capabilities.

Figure 39:
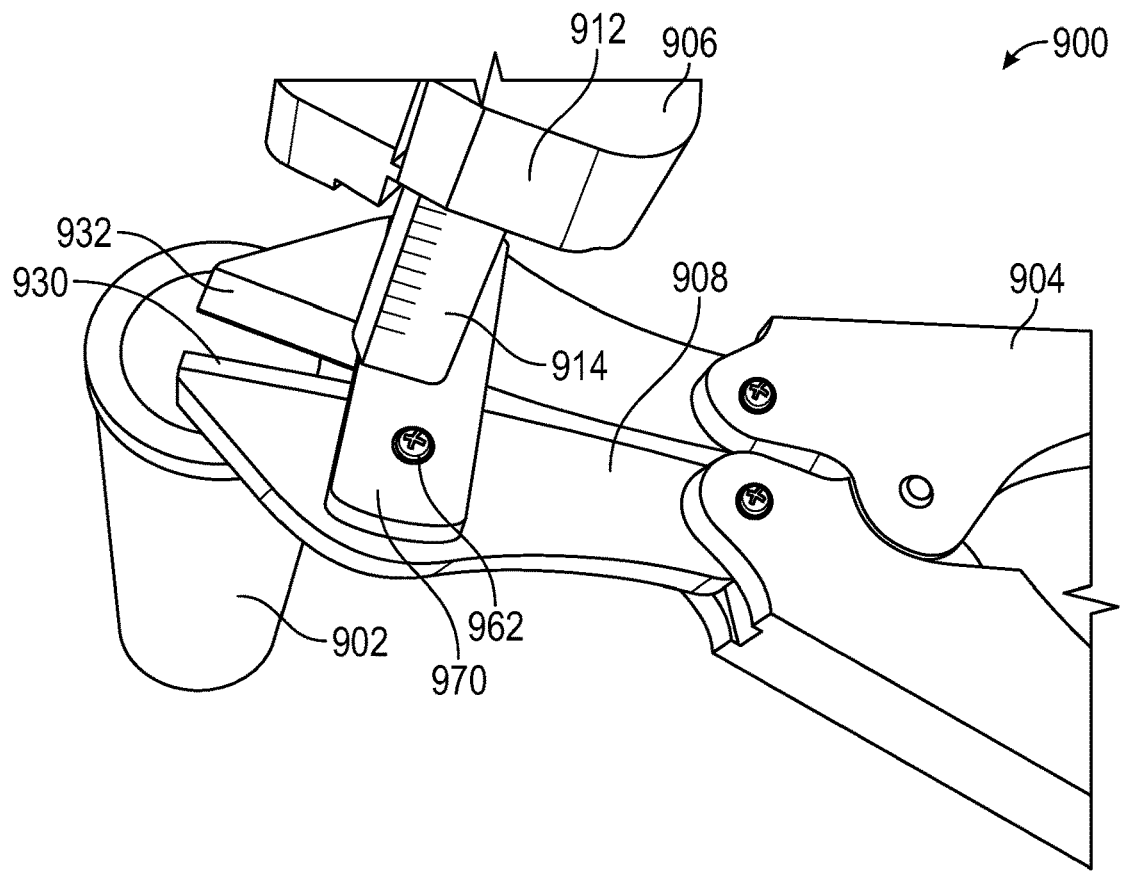
FIG. 39 is a magnified view of a first side of a cutting assembly of the system of FIG. 28.
Figure 40:
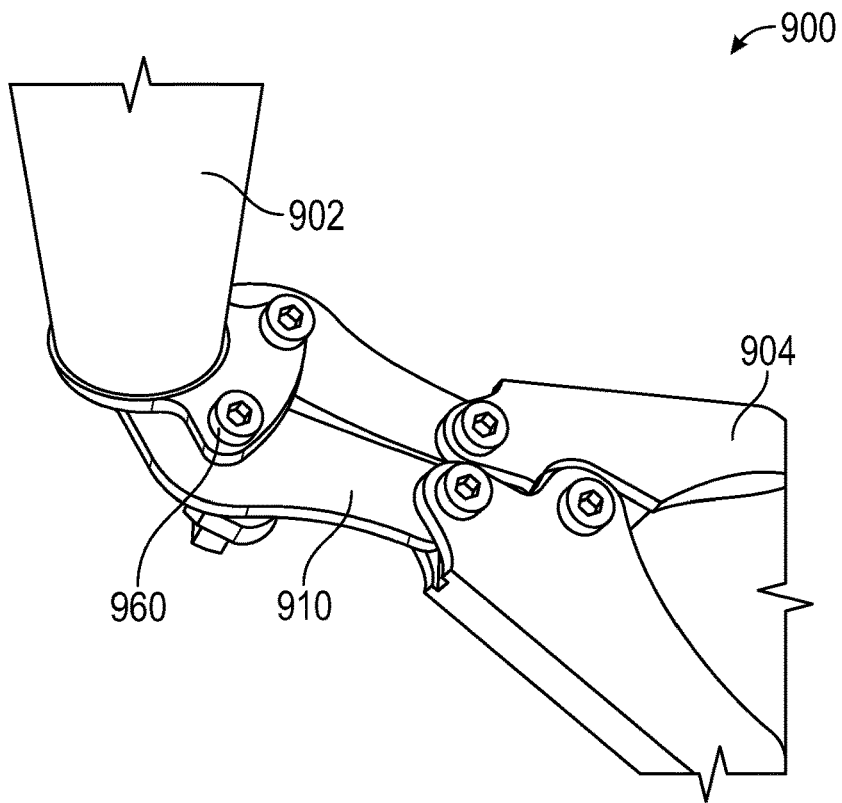
FIG. 40 is a magnified view of a second side of the cutting assembly of the system of FIG. 28.

In some embodiments, as shown in FIGS. 39 and 40, the cutting assembly 904 can be removable from (and thus removably coupled to) the container 902 and/or the position adjustment assembly 906. For example, in some embodiments, the cutting assembly 904 can be removably coupled to the container 902 by one or more first fasteners 960 (FIG. 40) and removably coupled to the position adjustment assembly 906 by one or more second fasteners 962 (FIG. 39). As a result, the blades 930 and 932 of the cutting assembly can be sharpened or replaced as needed.

An exemplary method of using the apparatus 900 to cut a bone screw blank, such as exemplary bone screw blank 950, to a specified length and create a self-tapping end portion on the cut bone screw 957, is described below with reference to FIGS. 30-34A.

During a surgical procedure, once an appropriate screw length is determined (e.g., by inserting a depth gauge into a hole drilled in the bone), the surgeon or a technician can select a bone screw blank of the appropriate type and size (e.g., bone screw blank 950, which can be any one of the bone screw blanks described herein). The cap 924 of the mounting member 912 can be pivoted away from the opening 922 in the second portion 920 (thereby moving the cap 924 into an open position) and the bone screw blank 950 can be inserted into the opening 922 such that the second end portion 955 (including a head) of the bone screw blank 950 is held within the mounting member 912 (FIG. 30). The cap 924 can then be pivoted over the opening 922, to enclose the second end portion 955 within the mounting member 912 (FIG. 31).

The mounting member 912 can then be moved along the measurement member 914, in a direction of the double-headed arrow 926, to a distance corresponding to the specified length for the cut bone screw (FIG. 32). In some embodiments, the inner edge 942 of the mounting member 912 can be aligned with the appropriate measurement marking 928 corresponding to the specified length for the cut bone screw.

The user can then operate and actuate the cutting assembly 904 (e.g., by squeezing the handles 934 and 336 together) such that the bone screw blank 950 is cut by the blades 930 and 932 (FIG. 33). The severed portion of the bone screw blank 950 can then be received in the container 902. In some embodiments, the container 902 can also be configured as a handle for the user to grip with one hand while operating the cutting assembly 904 with the other hand.

The cap 924 can then be pivoted back into an open position and the cut bone screw 957 can be removed from the apparatus 900. FIG. 36 shows an exemplary embodiment of the cut, first end portion 951 of the cut bone screw 957, after cutting is complete.

The first end portion 951 can then be honed (to better prepare it for insertion into a bone drill hole) by placing the first end portion 951 into the opening 948 in the cap 946 of the container 902 and rotating the cut bone screw 957 relative to the container 902 (e.g., with a screw driver, other tool, or by hand, as shown in FIG. 34A). The deburring member 952 within the cap 946 can create a honed, self-tapping end portion 953, as shown in FIG. 37. As shown in this figure, the self-tapping end portion 953 can have angled edges 956 that create a more narrowed edge 958 (as compared to the non-honed bone screw shown in FIG. 36) that can more easily self-thread into a drilled bone hole. Stated differently, the edges 956 can be angled inwardly toward the longitudinal axis of the cut bone screw 957 resulting in a tapered, honed, or pointed end and reduced length of the edge 958 as compared to the non-honed bone screw in FIG. 36.

Eighth Representative Embodiment

Figure 45:
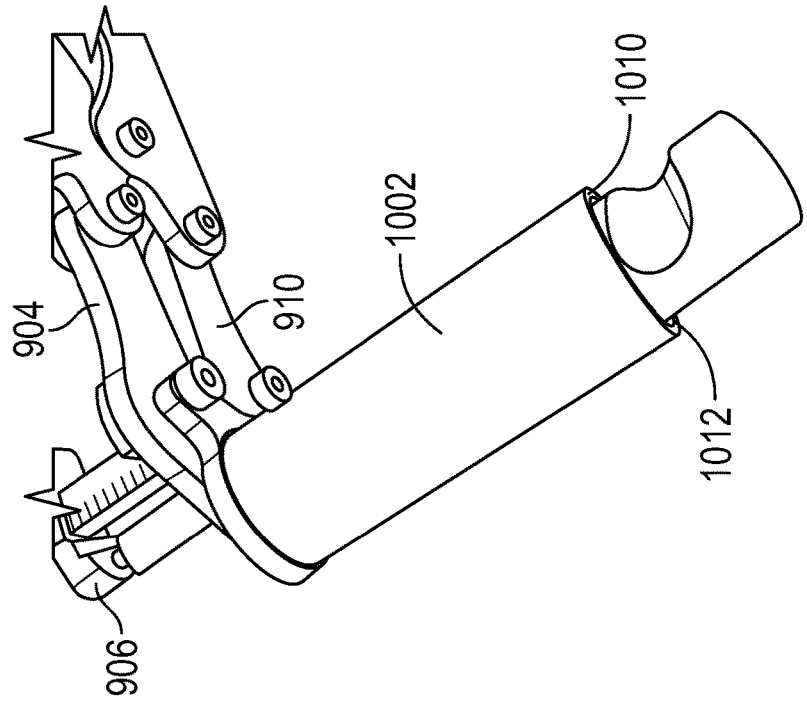
FIG. 45 is a second perspective view of the system of FIG. 44, illustrating a die cartridge coupled to the receptacle of the system.

FIGS. 44-47 illustrate another embodiment of a system, apparatus, or tool 1000 for positioning and cutting bone screw blanks to a specified length and forming a self-tapping end portion on the bone screws. The apparatus 1000 can include similar components to that of apparatus 900, and thus, common components have been labeled similarly in FIGS. 44-47. For example, the apparatus 1000 can comprise the cutting assembly 904, the position adjustment assembly 906, and a receptacle 1002 (the receptacle 1002 can also be referred to as a container or container portion). The position adjustment assembly 906 can be disposed on and coupled (e.g., removably coupled) to the first side 908 of the cutting assembly 904 (FIG. 44) and the receptacle 1002 can be disposed on and coupled (e.g., removably coupled) to the second side 910 of the cutting assembly 904 (FIG. 45).

Figure 44:
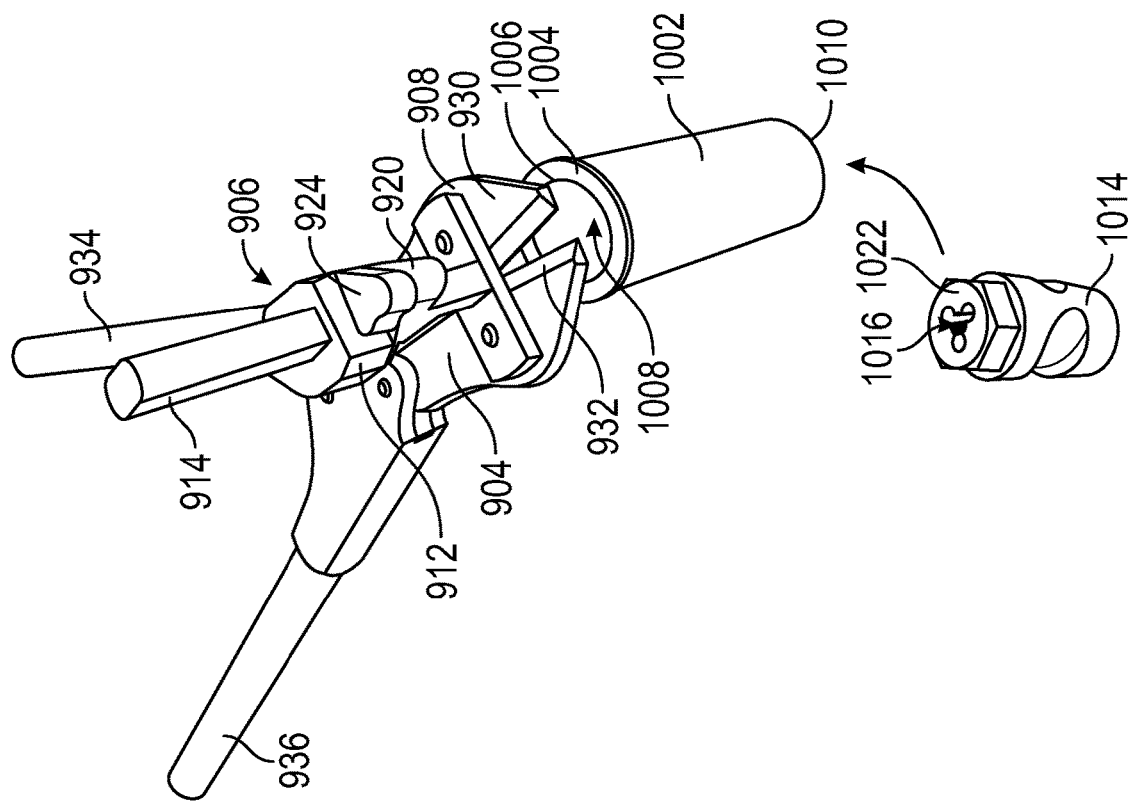
FIG. 44 is a first perspective view of another embodiment of a system for positioning and cutting a bone screw blank to a specified length and forming a self-tapping end portion on the resulting cut screw, illustrating a die cartridge removed from a receptacle of the system.
Figure 47:
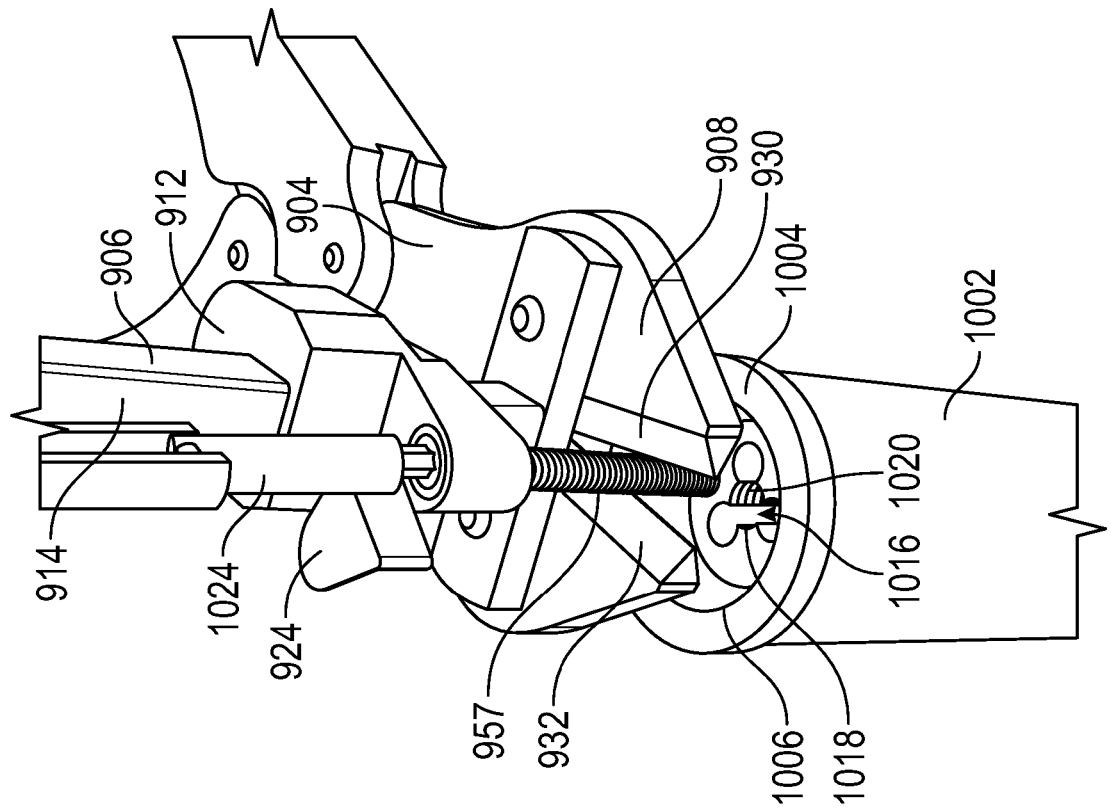
FIG. 47 is a magnified view of the system of FIG. 44, illustrating re-threading a cut end portion of a cut screw by advancing the cut end portion into the die cartridge through a cutting assembly of the system.
Figure 46:
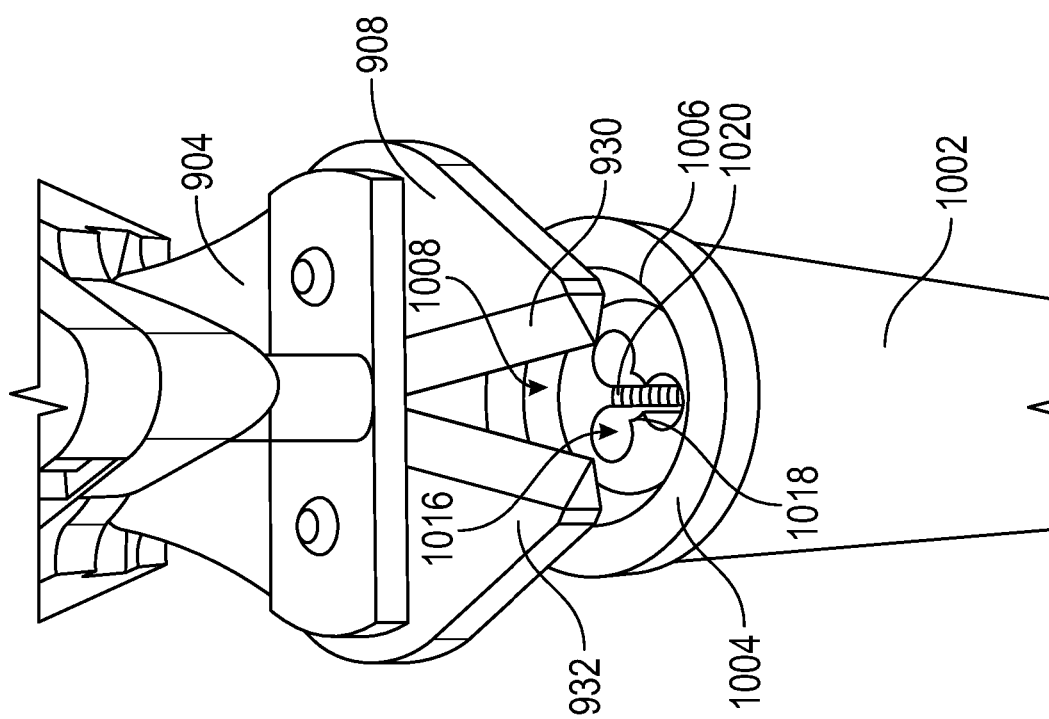
FIG. 46 is a magnified view illustrating a positioning of the die cartridge relative to a cutting assembly of the system of FIG. 44.

The receptacle 1002 can include a first end 1004 defining a first opening 1006 into an interior 1008 of the receptacle 1002 (FIGS. 44 and 46-47). The receptacle 1002 can further include a second end 1010, the second end 1010 disposed opposite the first end 1004, and defining a second opening 1012 (FIGS. 44 and 45).

The apparatus 1000 can further comprise a die cartridge 1014 which includes a threaded portion (e.g., die) 1016 including a central aperture 1018 with a plurality of threads 1020 (FIGS. 46 and 47). The central aperture 1018 is configured to receive the cut, first end portion 951 of the cut bone screw 957 and the threads 1020 can be configured to reform threads on the cut, first end portion 951 of the cut bone screw 957, after cutting. In some embodiments, the threads 1020 can be the same (e.g., same pitch and geometry) as the threads of the bone screw blank 950, thereby allowing the first end portion 951 to be re-threaded after cutting with the cutting apparatus 904 (as described above for apparatus 900).

As shown in FIGS. 44-47, the die cartridge 1014 can be inserted into the second end 1010 of the receptacle 1002, with an end 1022 of the die cartridge 1014 including the threaded portion 1016 inserted first. The end 1022 of the die cartridge 1014 including the threaded portion 1016 can be arranged adjacent to (e.g., below in FIGS. 46 and 47) the blades 930 and 932 of the cutting assembly 904 such that as a bone screw blank is advanced along its axis it passes between the blades 930 and 932 and into the receptacle 1002 to the threaded portion 1016 of the die cartridge 1014.

Figure 48:
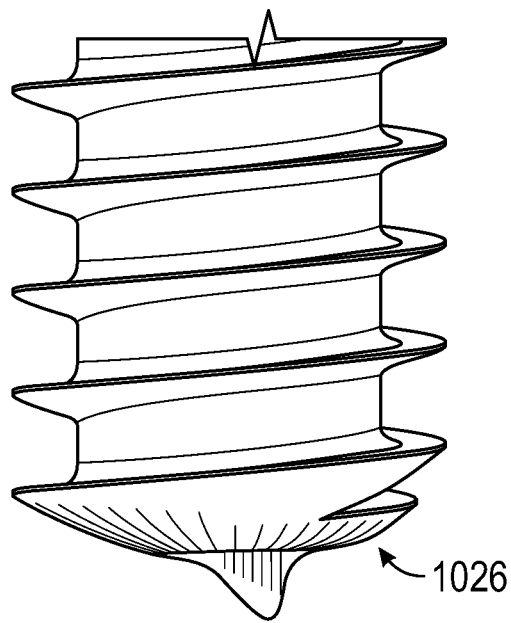
FIG. 48 is a first side view of an exemplary cut screw after being cut and re-threaded with the system of FIG. 44.
Figure 49:
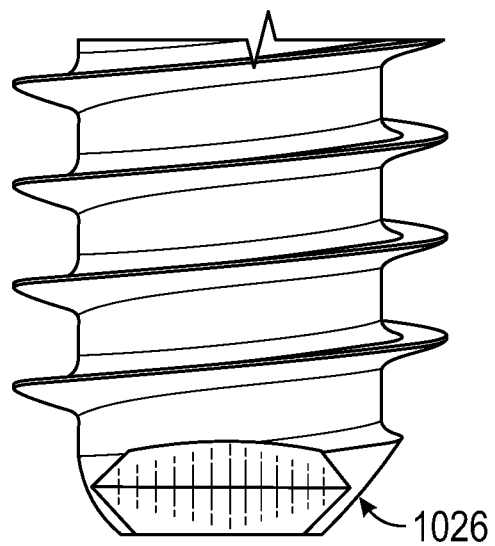
FIG. 49 is a second side view of the exemplary screw of FIG. 48 rotated about the longitudinal axis by 90°, illustrating a self-tapping end portion of the screw blank.

During use, the apparatus 1000 can be operated in a same or similar manner to that of apparatus 900 (as described above). However, after cutting the bone screw blank 950 to the specified length, the cut, first end portion 951 of the cut bone screw 957 can be advanced between the blades 930 and 932 and into the central aperture 1018 of the threaded portion 1016. The cap 924 can then be pivoted to reveal the head of the cut bone screw 957. A tool (e.g., screw driver) 1024 can then engage the head of the cut bone screw 957 and rotate the first end portion 951 within the threaded portion 1016 of the die cartridge 1014, thereby shaping and/or reforming the threads in the first end portion 951 of the cut bone screw 957 and creating a threaded, self-tapping end portion 1026 (FIGS. 48 and 49). In certain embodiments, the resulting cut bone screw can have a honed or tapered end portion similar to the bone screw of FIG. 37.

In some embodiments, the die cartridge 1014 can be shaped such that cut or severed pieces of the bone screw blank 950 (e.g., after cutting, as described above) can move through or past the die cartridge 1014 and into the receptacle 1002. For example, an embodiment of a die cartridge 1050 that can be inserted into the receptacle 1002 and used in the same way as the die cartridge 1014 (as described above) and which includes reliefs, recesses, slots, or depressions 1054 is shown in FIG. 54.

Figure 54:
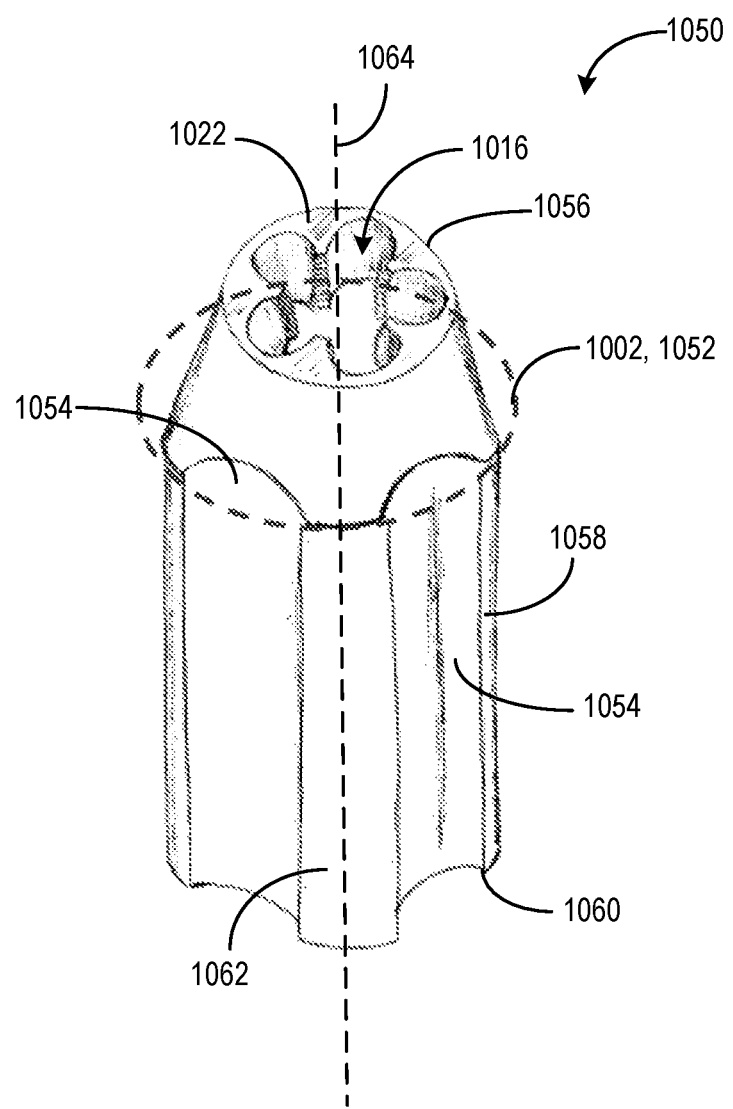
FIG. 54 is a perspective view of another embodiment of a die cartridge for the system of FIG. 44 which includes reliefs, slots, or depressions configured to receive severed tips of a bone screw blank therethrough.

For example, as shown in FIG. 54, a first end 1022 of the die cartridge 1050 including the threaded portion 1016 can have a smaller, first diameter 1056. A second portion (or body) 1058 of the die cartridge 1050 which extends to a second end 1060 of the die cartridge 1050 has a larger, second diameter 1052. In some embodiments, the second diameter 1052 can be shaped to fit within an inner diameter of the receptacle 1002. In this way, the second diameter 1052 can be the same or slightly smaller than the inner diameter of the receptacle 1002. An outer diameter of the die cartridge 1050 can increase from the first diameter 1056 at the first end 1022 to the second diameter 1052 at the second portion 1058 forming a tapered end portion.

The depressions 1054 can be formed or depressed into an outer surface 1062 of the second portion 1058 of the die cartridge 1050. For example, as shown in FIG. 54, each depression 1054 can be depressed radially inward, toward a central longitudinal axis 1064 of the die cartridge 1050, from the outer surface 1062. The die cartridge 1050 can include a plurality of depressions 1054 that are spaced apart from one another around a circumference of the die cartridge 1050.

As shown in FIG. 54, a cross-section of each of the depressions 1054 is semi-circular in shape. However, in other embodiments, the depressions 1054 can have a different cross-sectional shape, such as square, rectangular, triangular, and the like. The depressions can also have any suitable depth.

During use, when the die cartridge 1050 is arranged within the receptacle 1002 (e.g., as shown in FIGS. 46 and 47) and after cutting a bone screw blank with the cutting assembly 904, the severed tip of the bone screw blank can pass between an inner surface of the receptacle 1002 and a surface of one of the depressions 1054 (e.g., through a space or cavity created between the surface of the depression 1054 and the inner surface of the receptacle 1002) and into the receptacle 1002. In certain embodiments, the tapered walls of the first end portion can guide the severed screw tip toward the depressions. In this way, cut or severed tips of the bone screw blanks can be caught and contained within the receptacle 1002.

Ninth Representative Embodiment

Figure 52:
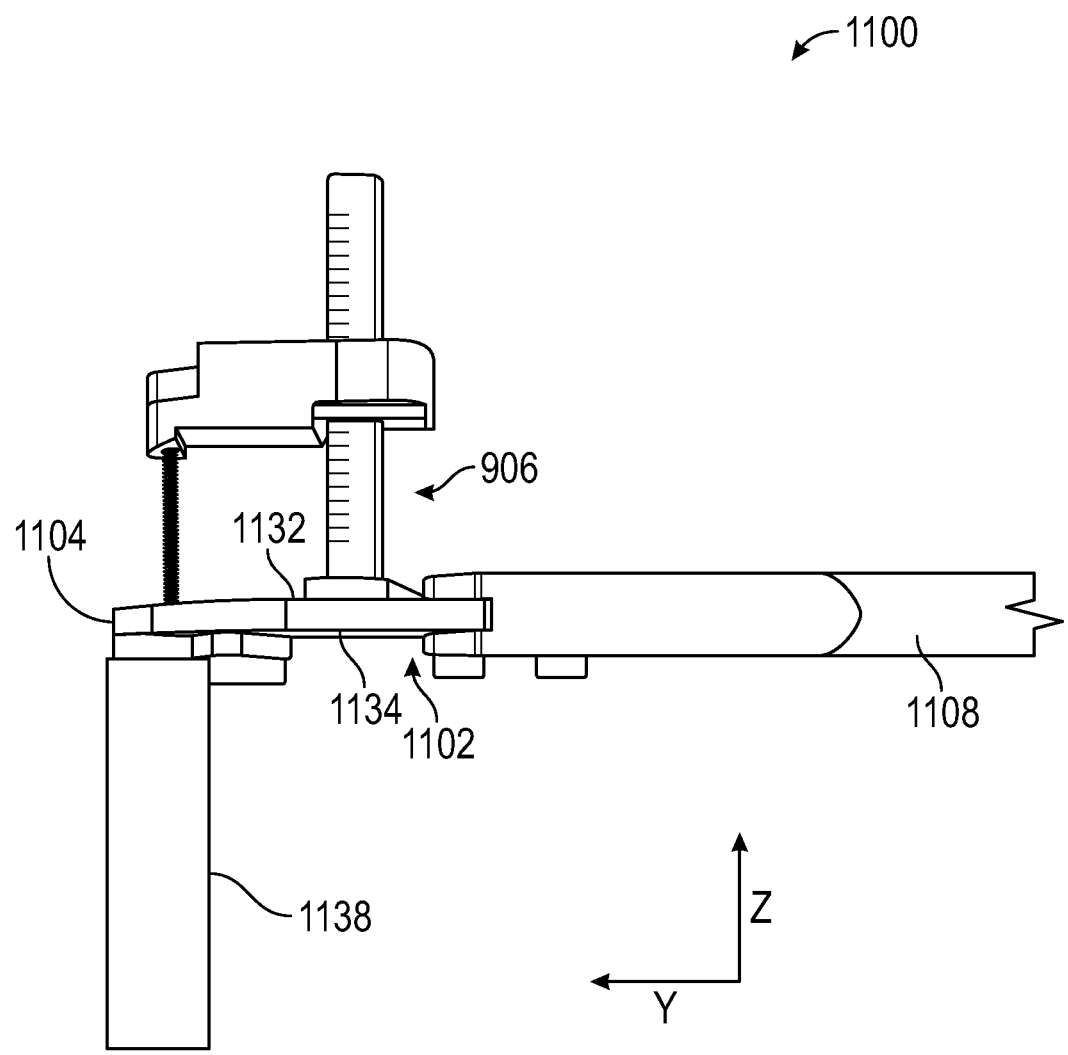
FIG. 52 is a side view of an embodiment of the system of FIG. 50.

FIGS. 50-52 illustrate another embodiment of a system, apparatus, or tool 1100 for positioning and cutting bone screw blanks to a specified length and forming a self-tapping end portion on the bone screws. The apparatus 1100 can comprise a cutting assembly 1102. The cutting assembly 1102 can comprise a cutting head (or mechanism) 1104 including a plurality of blades 1106. The cutting assembly 1102 can further comprise one or more actuation members, which can be configured as handles 1108 and 1110. The handles 1108 and 1110 can be configured to actuate the plurality of blades 1106 from and open position (FIG. 50) where a central opening or gap 1112 is formed between (and defined by) all the blades 1106 to a closed position (FIG. 51) where the gap 1112 is reduced, closed, or eliminated. For example, as shown in FIG. 51, the gap 1112 is closed by the blades 1106 in the closed position.

The cutting assembly 1102 can includes at least three blades 1106. In some embodiments, as shown in FIGS. 50 and 51, the cutting assembly 1102 includes three blades 1106. In other embodiments, the cutting assembly 1102 can include more than three blades 1106.

The three blades 1106 are arranged in a same plane (e.g., an x-y plane, as shown by the axes in FIG. 50). Further, the blades 1106 can be arranged or arrayed around a circumference or perimeter of the cutting head 1104, such that the blades 1106 are arranged in a circle on the cutting head 1104. In certain embodiments, the blades 1106 can be configured to move together or converge to close the central opening 1112 in the manner of a mechanical iris.

For example, in certain embodiments, each blade 1106 can comprise a first bearing or sliding surface 1118 that faces the central gap 1112 (in the open position of FIG. 50) and a center 1120 of the cutting head 1104. Further, the first sliding surface 1118 is disposed or extends between a first end 1114 and second end 1116 of the blade 1106, the first and second ends disposed opposite one another. The first sliding surface 1118 can include a cutting edge 1122 configured to cut the end portion of the bone screw blank received within the central gap 1112. The first sliding surface 1118 can be inwardly sloped toward the center 1120 of the cutting head 1104.

The first sliding surface 1118 of each blade 1106 is configured to translate or slide along the first end 1114 of an adjacent blade 1106 when moving from the open position (FIG. 50) to the closed position (FIG. 51). In the closed position (FIG. 51) the second ends 1116 of each blade 1106 are disposed closer to an outer perimeter 1124 of the cutting head 1104 than when in the open position (FIG. 50). Further, in the closed position (FIG. 51), the first ends 1114 of the blades 1106 are disposed closer together (thereby closing the central gap 1112) than in the open position (FIG. 50).

In some embodiments, each of the blades 1106 can be coupled to an outer gear configured to rotate around the cutting head 1104 upon actuation of the handles 1108, 1110. For example, each blade 1106 can be coupled to the outer gear by a connection between a first coupling element 1126 on the blade 1106 and a second coupling element 1128 that is connected to the underlying outer gear. For example, the outer gear can be covered by section 1130 shown in FIGS. 50 and 51.

In another embodiment, each of the blades 1106 can be coupled to a rotatable plate disposed in the cutting head 1104, the rotatable plate configured to rotate around the cutting head 1104 upon actuation of the handles 1108, 1110. For example, one of the handles 1108, 1110 can be coupled to the rotatable plate. Further, the rotatable plate can include a plurality of pin members or posts, where each post is received in or protrudes into a slot disposed in each blade 1106. In certain embodiments, the slots defined in the blades 1106 can be curved or angled. Movement of the posts in the slots, due to rotation of the rotatable plate, can cause the blades 1106 to move and converge to the center 1120, as shown in FIG. 51. In certain embodiments, the rotatable plate can be disposed at or covered by section 1130 shown in FIGS. 50 and 51.

In use, a first end portion of a bone screw blank can be received within the central gap 1112. In some embodiments, as shown in FIG. 52, the apparatus 1100 can further comprise a position adjustment assembly 906 that receives a second end portion (e.g., a head portion) of the bone screw blank and positions the bone screw blank at a specified distance from the cutting assembly 1102 (e.g., the first end portion to be cut may extend through the gap 1112, from a first side 1132 to an opposite, second side 1134 of the cutting assembly 1102). For example, the position adjustment assembly 906 (as described in detail above) can be coupled to the first side 1132 of the cutting assembly 1102.

Once the bone screw blank is secured in the specified position, the handles 1108 and 1110 can then be actuated (e.g., moved toward one another) to actuate the blades 1106 to move or converge from the open position (FIG. 50) to the closed position (FIG. 51), thereby closing the gap 1112 and cutting the first end portion of the bone screw blank.

In some embodiments, as shown in FIG. 52, the apparatus 1100 can further comprise a receptacle or container (e.g., container portion) 1138 coupled to the second side 1134 of the cutting assembly 1102 and configured to receive (and catch) the cut portion of the bone screw blank after cutting. In other embodiments, the apparatus 1100 may not include the container 1138.

Figure 53A:
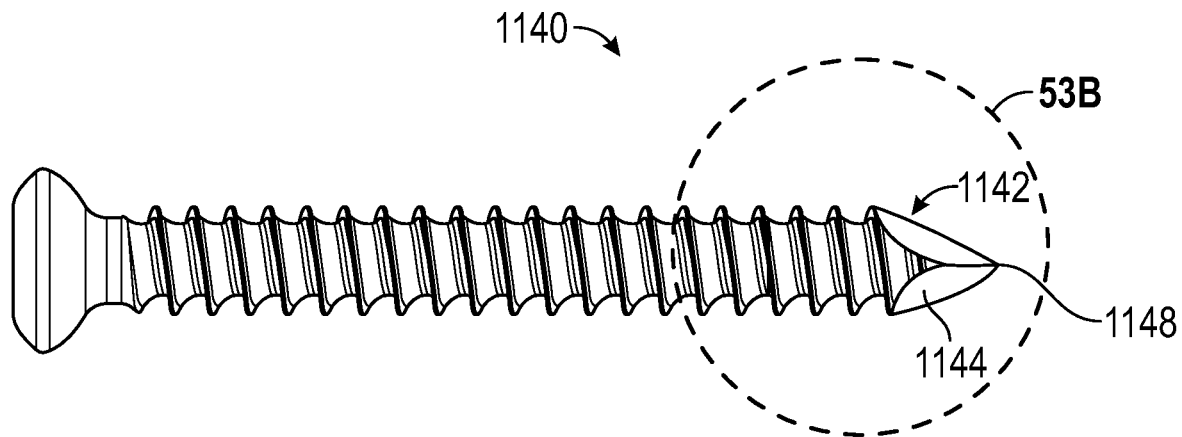
FIG. 53A is a side view of an exemplary cut screw with a self-tapping end portion formed with the cutting assembly of the system of FIG. 50.
Figure 53B:
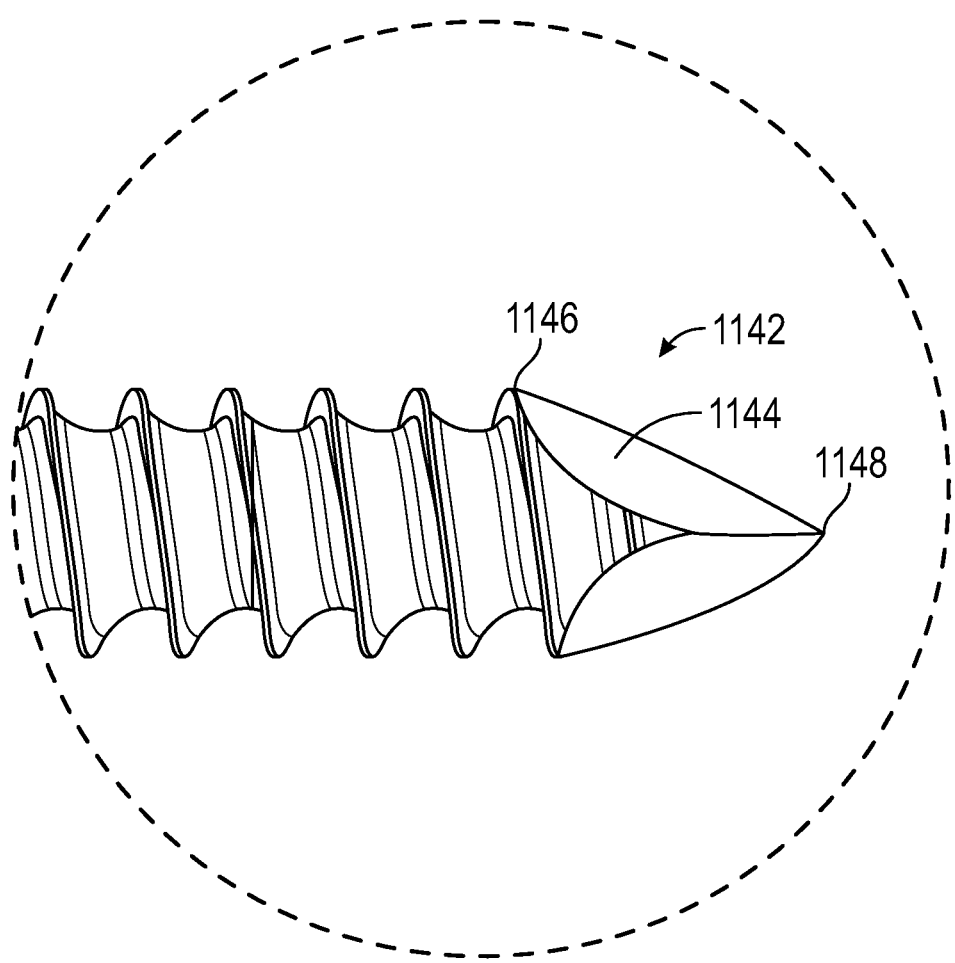
FIG. 53B is a magnified view of the screw of FIG. 53A.

An exemplary cut bone screw 1140 that can be formed using the apparatus 1100, as described above, is shown in FIGS. 53A and 53B. The cut bone screw 1140 includes a cut, self-tapping end portion 1142 which includes a plurality of angled or sloped surfaces 1144 that each angle inwardly from an outer surface 1146 of the cut bone screw 1140 to a point 1148 of the cut bone screw 1140, the point 1148 disposed at an end of the self-tapping end portion 1142. In some embodiments, the shape of the self-tapping end portion 1142 can be referred to as an at least three-sided cutting point or a trocar point. In the embodiment shown in FIGS. 53A and 53B, the resulting self-tapping end portion 1142 includes three sloped surfaces 1144, each created by one of the blades 1106. In some embodiments, each of the sloped surfaces 1144 can be relatively planar and/or smooth. The sloped surfaces 1144 and point 1148 may enhance the self-tapping capabilities of the resulting cut bone screw 1140, thereby enabling it to be more easily inserted into a bone hole or bore and self-form threads therein.

As compared to other embodiments described herein, the apparatus 1100 can create a finished, self-tapping end portion 1142 in a single step (e.g., the cutting step described above), without additional deburring, honing, or re-forming of threads.

Though the above-described embodiments of screw cutting systems and related components are described with reference to systems and methods for cutting bone screw blanks, any of the systems and/or methods described herein can also be applicable to receive and cut other types of screws (e.g., non-bone screws, wood screws, sheet metal screws, and the like).

One or more of the embodiments described herein can provide significant advantages over known systems and methods of preparing for and conducting orthopedic surgical procedures. For example, the systems and methods described herein can reduce or eliminate the need to autoclave or sterilize multiple surgical packs including tens or hundreds of bone screws of different types, sizes, lengths, etc., before every surgery, and to restock hardware that was not used during a procedure. This can also reduce the need and associated cost of keeping hundreds or thousands of such bone screws in inventory, especially unusual lengths, because the bone screws can be cut to length and/or tapped intraoperatively according to the needs of the particular patient. Such advantages can be especially significant in veterinary orthopedics, in which there are many "mobile" surgeons who perform procedures such as fracture fixation and TPLOs for multiple hospitals. Such surgeons travel from hospital to hospital, and often must bring their implants and instruments with them, including the large inventory of bone screws noted above.

The surgical kits described herein, in combination with the bone screw preparation systems and methods, can also save a significant amount of time that would otherwise be required to gather the bone screw inventory for a particular procedure, and sterilize the bone screws and the implant before surgery. With the kits described herein, the sterilized implant and bone screws can be retrieved from the kit package in the operating room, and no pre-sterilization is required. This can reduce or eliminate the need for hospitals/clinics to organize the multiple trays typically required for the variety of bone screws and implants of a particular procedure. This can also reduce the administrative burden of ordering and replacing bone screws from an extensive inventory as they are used, reduce the number of items that must be sterilized pre-operatively, and reduce the time and administrative burden of storage and retrieval of sterilized products, offering significant time and cost savings for hospitals/clinics. Additionally, quality control over surgical asepsis can be improved because the implant and bone screws of the kit are pre-sterilized by the manufacturer.

Further, the cutting systems and/or apparatuses described herein can provide a precise and efficient way of cutting bone screw blanks to a specified length, creating a self-tapping end portion on the cut bone screws, and finishing the self-tapping end portion to have enhanced self-tapping capabilities, all with one integrated tool or apparatus. Further, in some embodiments, a cut bone screw blank with a refined, self-tapping end portion can be created in one step (e.g., a single cut without needing to further shave, hone, re-thread, or otherwise finish or refine) with such an apparatus.

Explanation of Terms

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

As used in this disclosure and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

Unless otherwise indicated, all numbers expressing angles, dimensions, quantities of components, forces, moments, molecular weights, percentages, times, and so forth, as used in the specification or claims are to be understood as being modified by the term "about." Accordingly, unless otherwise indicated, implicitly or explicitly, the numerical parameters set forth are approximations that can depend on the desired properties sought and/or limits of detection under test conditions/methods familiar to those of ordinary skill in the art. When directly and explicitly distinguishing embodiments from discussed prior art, the embodiment numbers are not approximates unless the word "about" is recited. Furthermore, not all alternatives recited herein are equivalents.

Although there are alternatives for various components, parameters, operating conditions, etc., set forth herein, that does not mean that those alternatives are necessarily equivalent and/or perform equally well. Nor does it mean that the alternatives are listed in a preferred order unless stated otherwise.

In view of the many possible embodiments to which the principles of the disclosed technology may be applied, it should be recognized that the illustrated embodiments are only examples and should not be taken as limiting the scope of the disclosure. Rather, the scope of the disclosure is at least as broad as the following claims. We therefore claim all that comes within the scope and spirit of these claims.

The invention claimed is:

1. A bone screw cutting system, comprising:
   a cutting assembly comprising a plurality of blades; and
   a position adjustment assembly coupled to the cutting assembly and configured to receive a bone screw blank and position the bone screw blank relative to the cutting assembly;
   wherein the cutting assembly is configured to cut the bone screw blank received by the position adjustment assembly and to form a self-tapping end portion at a cut end of the bone screw blank, thereby resulting in a cut bone screw.

2. The system of claim 1, wherein the position adjustment assembly includes a mounting member and a measurement member, the mounting member configured to slide along a length of the measurement member, relative to the cutting assembly, and receive an end portion of the bone screw blank that is arranged opposite an end portion of the bone screw blank to be cut by the cutting assembly.

3. The system of claim 1, further comprising a container portion configured to receive severed portions of bone screw blanks cut with the cutting assembly.

4. The system of claim 3, wherein the position adjustment assembly is coupled to a first side of the cutting assembly and the container portion is coupled to a second side of the cutting assembly, opposite the first side.

5. The system of claim 4, wherein the container portion includes a first end coupled to the second side of the cutting assembly and wherein a cap including a deburring member is removably coupled to a second end of the container portion, the deburring member configured to hone the self-taping end portion of the cut bone screw.

6. The system of claim 1, wherein the position adjustment assembly is coupled to a first side of the cutting assembly and further comprising a receptacle coupled to a second side of the cutting assembly, the second side opposite to the first side, and wherein a die cartridge including a threaded portion is disposed within the receptacle, with the threaded portion disposed adjacent the plurality of blades of the cutting assembly, the threaded portion configured to reform threads at the cut end of the bone screw blank to further form the self-tapping end portion.

7. The system of claim 1, wherein the plurality of blades includes at least three blades arranged in a plane defined by a cutting head of the cutting assembly, the at least three blades configured to move from an open position to a closed position, wherein in the open position a central gap is defined between the three blades, and wherein in the closed position the blades converge such that the gap is closed such that an end portion of the bone screw blank received in the central gap is cut into an at least three-sided cutting point that forms the self-tapping end portion.

8. The system of claim 7, wherein each blade of the at least three blades includes a first sliding surface disposed between a first end and second end of the blade, the first and second ends disposed opposite one another, and wherein the first sliding surface includes a cutting edge configured to cut the end portion of the bone screw blank.

9. The system of claim 8, wherein the first sliding surface is configured to slide along the first end of an adjacent blade of the at least three blades when moving from the open position to the closed position and wherein in the closed position the second end of each blade is disposed closer to an outer perimeter of the cutting head than when in the open position.

10. The system of claim 7, wherein the cutting assembly further comprises two opposing handles coupled to a rotatable plate of the cutting head and configured to actuate the plurality of blades to move from the open position to the closed position.

11. The system of claim 1, wherein the cutting assembly further comprises two opposing handles coupled to the plurality of blades and configured to actuate the plurality of blades to cut the bone screw blank.

12. The system of claim 1, wherein the blades of the cutting assembly comprise radiused edges.

13. The system of claim 1, wherein the blades of the cutting assembly are tapered to fit between threads of the bone screw blank.

14. A bone screw cutting system, comprising:
- a cutting assembly comprising a plurality of blades configured to converge toward one another in a same plane from an open position to a closed position, wherein in the open position a central opening is formed between the plurality of blades and in the closed position the central opening is closed; and
- a position adjustment assembly configured to receive a bone screw blank and position the bone screw blank relative to the cutting assembly;
- wherein the cutting assembly is configured to cut the bone screw blank received by the position adjustment assembly and to form a self-tapping end portion at a cut end of the bone screw blank, thereby resulting in a cut bone screw.

15. The system of claim 14, wherein the self-tapping end portion is configured to be self-tapping and self-form threads inside a drilled hole.

16. The system of claim 14, wherein the self-tapping end portion is an at least three-sided cutting point, wherein each blade of the plurality of blades includes a first sliding surface disposed between a first end and second end of the blade, the first and second ends disposed opposite one another, and wherein the first sliding surface includes a cutting edge configured to cut the bone screw blank and form one side of the at least three-sided cutting point.

17. The system of claim 16, wherein the first sliding surface is configured to slide along the first end of an adjacent blade of the plurality of blades when moving from the open position to the closed position and wherein in the closed position the second end of each blade is disposed closer to an outer perimeter of the cutting assembly than when in the open position.

18. A bone screw cutting system, comprising:
- a cutting assembly comprising at least three blades arranged in a circle on a cutting head of the cutting assembly, the at least three blades movable between an open position where a central aperture is formed between the at least three blades, the central aperture configured to receive a first end portion of a bone screw blank, and a closed position where the central aperture is closed by the at least three blades; and
- a position adjustment assembly configured to receive a second end portion of the bone screw blank and position the bone screw blank relative to the cutting assembly, the second end portion disposed opposite the first end portion,
- wherein the cutting assembly is configured to cut the first end portion of the bone screw blank received within the central aperture and to form an at least three-sided cutting point at the first end portion, thereby resulting in a cut bone screw with a self-tapping end portion.

19. The system of claim 18, wherein each blade of the at least three blades includes a sliding surface with a cutting edge disposed between a first end and a second end of the blade and wherein in the closed position first ends of the blades converge together to close the central aperture and second ends of the blades are disposed closer to a perimeter of the cutting head than when in the open position.

* * * * *